United States Patent
Zeng et al.

(10) Patent No.: US 9,654,745 B2
(45) Date of Patent: May 16, 2017

(54) RAPID MULTI-SPECTRAL IMAGING METHODS AND APPARATUS AND APPLICATIONS FOR CANCER DETECTION AND LOCALIZATION

(76) Inventors: Haishan Zeng, Vancouver (CA); Yasser Fawzy, Vancouver (CA)

( * ) Notice: Subject to any disclaimer, the term of this patent is extended or adjusted under 35 U.S.C. 154(b) by 758 days.

(21) Appl. No.: 13/635,682

(22) PCT Filed: Mar. 17, 2011

(86) PCT No.: PCT/CA2011/050148
§ 371 (c)(1),
(2), (4) Date: Sep. 17, 2012

(87) PCT Pub. No.: WO2011/113162
PCT Pub. Date: Sep. 22, 2011

(65) Prior Publication Data
US 2013/0012794 A1  Jan. 10, 2013

Related U.S. Application Data

(60) Provisional application No. 61/314,893, filed on Mar. 17, 2010.

(51) Int. Cl.
*A61B 1/06* (2006.01)
*A61B 5/00* (2006.01)
(Continued)

(52) U.S. Cl.
CPC ......... *H04N 9/045* (2013.01); *A61B 1/00186* (2013.01); *A61B 1/043* (2013.01);
(Continued)

(58) Field of Classification Search
CPC . A61B 1/00186; A61B 1/0646; A61B 1/0638; A61B 5/0075; A61B 1/043;
(Continued)

(56) References Cited

U.S. PATENT DOCUMENTS 5,749,830 A * 5/1998 Kaneko ............. A61B 1/00082
348/E5.038
5,796,512 A 8/1998 Wachman et al.
(Continued)

FOREIGN PATENT DOCUMENTS

CN 100569177 C 12/2009
EP 1528380 A1 5/2005
(Continued)

OTHER PUBLICATIONS

Hernandez, S. E. et al., Diffuse reflectance spectroscopy characterization of hemoglobin and intralipid solutions: in vitro measurements with continuous variation of absorption and scattering, JBO 14(3), 034026 (2009).

(Continued)

*Primary Examiner* — Katherine Fernandez
*Assistant Examiner* — Angela M Hoffa
(74) *Attorney, Agent, or Firm* — Oyen Wiggs Green & Mutala LLP

(57) ABSTRACT

Methods and apparatus for video rate or near video rate quantitative imaging of tissue physiological and morphological properties from visible/NIR light spectral images obtain rapid multi-spectral reflectance images by illuminating with a series of spectra containing multiple narrow wavelength bands. An iterative light-transport based inversion algorithm may be applied for correcting the intensity of the spectral images from the geometry/coupling effect as well as from the scattering amplitude distortions. The method can produce video rate absorption as well as scattering spectral images that can be further analyzed very rapidly, using matrix-based rapid inversion algorithms to produce more detailed quantitative images containing information relevant to tissue physiology and morphology.

49 Claims, 16 Drawing Sheets

(51) Int. Cl.

| | |
|---|---|
| H04N 9/04 | (2006.01) |
| A61B 1/00 | (2006.01) |
| G01J 3/10 | (2006.01) |
| G01J 3/28 | (2006.01) |
| G01J 3/36 | (2006.01) |
| H04N 5/33 | (2006.01) |
| A61B 1/04 | (2006.01) |
| H04N 5/225 | (2006.01) |

(52) U.S. Cl.
CPC .......... *A61B 1/0638* (2013.01); *A61B 1/0646* (2013.01); *A61B 1/0684* (2013.01); *G01J 3/10* (2013.01); *G01J 3/28* (2013.01); *G01J 3/36* (2013.01); *H04N 5/332* (2013.01); *A61B 1/0607* (2013.01); *A61B 1/0676* (2013.01); *A61B 5/0059* (2013.01); *G01J 2003/2866* (2013.01); *H04N 2005/2255* (2013.01)

(58) Field of Classification Search
CPC ... A61B 1/0684; A61B 1/0607; A61B 1/0676; G01J 3/10; G01J 3/2826; G01J 3/36; G01J 3/28; G01J 2003/2866; H04N 5/332; H04N 9/045; H04N 2005/2255
See application file for complete search history.

(56) References Cited

U.S. PATENT DOCUMENTS

| | | | |
|---|---|---|---|
| 6,061,591 A | | 5/2000 | Freitag et al. |
| 6,069,689 A | * | 5/2000 | Zeng et al. ............... 356/73 |
| 6,081,612 A | | 6/2000 | Gutkowicz-Krusin et al. |
| 6,678,398 B2 | | 1/2004 | Wolters et al. |
| 6,697,652 B2 | * | 2/2004 | Georgakoudi et al. ....... 600/310 |
| 6,826,424 B1 | | 11/2004 | Zeng et al. |
| 6,898,458 B2 | | 5/2005 | Zeng et al. |
| 7,321,791 B2 | * | 1/2008 | Levenson ............ A61B 5/0059 356/432 |
| 7,729,751 B2 | | 6/2010 | Ayame et al. |
| 8,391,961 B2 | * | 3/2013 | Levenson ............ A61B 5/0059 356/300 |
| 2002/0103439 A1 | * | 8/2002 | Zeng et al. .................. 600/476 |
| 2004/0225222 A1 | | 11/2004 | Zeng et al. |
| 2004/0245350 A1 | * | 12/2004 | Zeng ............... 236/43 |
| 2005/0059894 A1 | * | 3/2005 | Zeng et al. .................. 600/476 |
| 2006/0152586 A1 | | 7/2006 | Komiya et al. |
| 2006/0264760 A1 | * | 11/2006 | Liu et al. ..................... 600/473 |
| 2007/0024946 A1 | | 2/2007 | Panasyuk et al. |
| 2007/0167836 A1 | * | 7/2007 | Scepanovic et al. ......... 600/476 |
| 2008/0208006 A1 | | 8/2008 | Farr |
| 2009/0023991 A1 | | 1/2009 | Gono et al. |
| 2009/0137908 A1 | | 5/2009 | Patwardhan |
| 2009/0225156 A1 | * | 9/2009 | Akiyama et al. ............... 348/68 |
| 2009/0270702 A1 | | 10/2009 | Zeng et al. |
| 2010/0033986 A1 | | 2/2010 | Schober et al. |
| 2010/0056928 A1 | | 3/2010 | Zuzak et al. |
| 2013/0300848 A1 | * | 11/2013 | Levenson ............ A61B 5/0059 348/68 |

FOREIGN PATENT DOCUMENTS

| | | |
|---|---|---|
| EP | 2332460 A1 | 6/2011 |
| JP | 2008-036035 A | 2/2008 |
| JP | 2008-283692 A | 11/2008 |
| WO | 2005088264 A1 | 9/2005 |
| WO | 2009018849 A1 | 2/2009 |
| WO | 2009052607 A1 | 4/2009 |

OTHER PUBLICATIONS

Hidovic-Rowe, D. et al., Modelling and validation of spectral reflectance for the colon, Phys. Med. Biol. 50 (2005) 1071-1093.

Li, Q. et al., Review of spectral imaging technology in biomedical engineering: achievements and challenges, JBO 18 (10), 100901 (2013).

Palero, J.A. et al., In vivo nonlinear spectral imaging in mouse skin, Opt. Exp. 2006; 14:4395-4402.

Lee, J.A. et al., Combination of spectral and fluorescence imaging microscopy for wide-field in vivo analysis of microvessel blood supply and oxygenation, Opt Lett. 2013; 38(3):332-334.

Bish, S.F. et al., Handheld diffuse reflectance spectral imaging (DRSi) for in-vivo characterization of skin, Biomed. Opt. Exp. 2014; 5: 573-586.

Brauers, J. et al., Multispectral Filter-Wheel Cameras: Geometric Distortion Model and Compensation Algorithms, IEEE Transactions on Image Processing, vol. 17, No. 12, Dec. 2008.

Gebhart, S.C. et al., Liquid-crystal tunable filter spectral imaging for brain tumor demarcation, App. Opt., vol. 46, No. 10, pp. 1896-1910 (2007).

Hardeberg, J.Y. et al., Multispectral image capture using a tunable filter, SPIE Proc., vol. 3963, pp. 77-88 (2008).

Martin, M.E. et al., Development of an Advanced Hyperspectral Imaging (HSI) System with Applications for Cancer Detection, Annals of Biomed. Eng. 2006; 34: 1061-1068.

Vo-Dinh, T. et al., Development of a multi-spectral imaging system for medical applications, J. Phys. D: Appl. Phys. 2003;36:1663-1668.

Gat, N., Imaging spectroscopy using tunable filters: A review, Proc.. SPIE vol. 4056, p. 50-64, 2000.

MacKinnon, N. et al., Spectrally programmable light engine for in vitro or in vivo molecular imaging and spectroscopy, Appl. Opt. 2005; 44:2033-2040.

Yokoyama, K. et al., Interpretation of principal components of the reflectance spectra obtained from multispectral images of exposed pig brain, JBO 2005; 10(1), 011005.

Tsumura, N. et al., Independent Component Analysis of Spectral Absorbance Images of Human Skin, Optical Review, vol. 7, No. 6, 479-482 (2000).

Ferris, D.G. et al., Multimodal Hyperspectral Imaging for the Noninvasive Diagnosis of Cervical Neoplasia, Journal of Lower Genital Tract Disease 2001;5 :65-72.

Claridge, E. et al., Quantifying mucosal blood volume fraction from multispectral images of the colon, SPIE Medical Imaging 2007, 17-22.

Jacques, S.L. et al., Rapid spectral analysis for spectral imaging, Biomed. Opt. Exp. 2010;1:157.

Stigell, P. et al., Estimation Method in Estimating of Spectral Reflectance from RGB Images Pattern Recognition and Image Analysis, 2007, vol. 17, No. 2, pp. 233-242.

Lisenko, S.A. et al., Method for determining skin pigment concentrations from multispectral images of the skin, Measurement Techniques 2013;56:721-729.

Vyas, S. et al., Estimating physiological skin parameters from hyperspectral signatures, J. Biomed. Opt. 2013;18:057008.

Mourant, J.R. et al., Evidence of intrinsic differences in the light scattering properties of tumorigenic and nontumorigenic cells, Cancer 84, 366-374 1998.

Zonios, G. et al., Diffuse reflectance spectroscopy of human adenomatous colon polyps in vivo, Appl.Opt.1998; 38:6628-6636.

Tsumura, N. et al., Mapping pigmentation in human skin by multivisible-spectral imaging by inverse optical scattering technique, J. Img. Sci. Tech. 2001; 45:444-450.

Kainerstorfer, J.M. et al., Principal component model of multispectral data for near real-time skin chromophore mapping, JBO 2010; 15: 046007.

Jolivot, R. et al., Skin parameter map retrieval from a dedicated multispectral imaging system applied to dermatology/cosmetology, Int J. of Biomedical Imaging 2013:978289.

Dhawan, A.P. et al., Analysis of multi-modal optical images of skin-lesions for skin-cancer detection and characterization, Proc. 5th Int. Conf. Information Technology and Applications in Biomedicine, ITAB 2008 in Conjunction with 2nd Int. Symp. Summer School Biomed. Health Eng., IS3BHE, 2008, pp. 62-65.

(56) References Cited

OTHER PUBLICATIONS

Patwardhan, S.V. et al., Monte Carlo simulation of light-tissue interaction: Three-dimensional simulation for trans-illumination-based imaging of skin lesions, IEEE Trans. Biomed. Eng. 2005; 52:1227-1236.
Balas, C. et al., A novel hyper-spectral imaging system: application on in-vivo detection and grading of cervical precancers and pigmented lesions, Proc. Computer Vision Beyond the Visible Spectrum (CVBVS' 01 workshop) Hawaii, USA [20] S. Tomatis, 2001.
Osawa, H. et al., Optimal band imaging system can facilitate detection of changes in depressed-type early gastric cancer, Gastrointestinal Endoscopy, 2008; 67: 226-234.
Balas, C., Review of biomedical optical imaging—a powerful, non-invasive, non-ionizing technology for improving in vivo diagnosis, Meas. Sci. Technol. 2009; 20: 104020, pp. 1-12.
Yamaguchi, M. et al., Video-Telemedicine with Reliable Color Based on Multispectral Technology Advances in Telemedicine: Technologies, Enabling Factors and Scenarios, ISBN: 978-953-307-159-6, 2011.
Yamaguchi, M. et al., Multispectral Color Imaging for Dermatology: Application in Inflammatory and Immunologic Diseases, Thirteenth Color Imaging Conference: Color Science and Engineering Systems, Technologies, and Applications Scottsdale, Arizona; Nov. 2005; p. 52-58.
Zeng, H. et al., Integrated Endoscopy System for Simultaneous Imaging and Spectroscopy for Early Lung Cancer Detection, Optics Letters, 2004; 29: 587-589.
Tsumura, N. et al., Limitation of Color Samples for Spectral Estimation from Sensor Responses in Fine Art Painting, Optical Review, 57-61, 1999.
Themelis, G. et al., "Real-time intraoperative fluorescence imaging system using light-absorption correction", Journal of Biomedical Optics, vol. 14(6), Nov./Dec. 2009.
Bradley, R.S. et al., "A review of attenuation correction techniques for tissue fluorescence", Journal of the Royal Society Interface, 3, 1-13, Aug. 25, 2006.
Bard, M.P.L. et al., "Measurement of Hypoxia-related parameters in bronchial mucosa by use of optical spectroscopy", Am. J. Respir. Crit. Care Med., 171, 1178-1184, 2005.
Zonios, G. et al., "Diffuse reflectance spectroscopy of human adenomatous colon polyps in vivo", Appl. Opt. 38, 6628-6637, 1999.
Beauvoit, B. et al., "Time-resolved spectroscopy of mitochondria, cells and tissue under normal and pathological conditions", Mol. Cell Biochem., 184, 445-455, 1998.
Mourant, J.R. et al., "Characterizing mammalian cells and cell phantoms by polarized backscattering fiber-optic measurement", Appl. Opt. 40, 5114-5123, 2001.
Mourant, J.R. et al., "Evidence of intrinsic differences in the light scattering properties of tumorigenic and nontumorigenic cells", Cancer, 84, 366-374, 1998.
Zeng, H. et al., "A computerized auto-fluorescence and diffuse reflectance spectroanalyser system for in vivo skin studies", Phys. Med. Biol. 38, 231-240, 1993.
Nordstorm, R.J. et al., "Identification of cervical intraepithelial neoplasia (CIN) using UV-excited fluorescence and diffuse-reflectance tissue spectroscopy", Lasers Surg. Med. 29, 118-127, 2001.
Georgakoudi, I. et al., "Trimodal spectroscopy for the detection and characterization of cervical precancers in vivo", Am J Obstet Gynecol 186, 374-382, 2002.
Mueller, M.G. et al., "Spectroscopic detection and evaluation of morphologic and biochemical changes in early human oral carcinoma", Cancer 97, 1681-1692, 2003.
Bard, M.P.L. et al., "Improving the specificity of fluorescence bronchoscopy for the analysis of neoplastic lesions of the bronchial tree by combination with optical spectroscopy: preliminary communication", Lung Cancer 47, 41-47, 2005.
Stamatas, G.N. et al., "In vivo monitoring of cutaneous edema using spectral imaging in the visible and near infrared", J. Invest. Dermatol. 126, 1753-1760, 2006.
Stamatas, G.N. et al., "Noninvasive quantitative documentation of cutaneous inflammation in vivo using spectral imaging", SPIE Proceedings 6078, 60780P, 2006.
Farkas, D.L. et al., "Applications of spectral imaging: detection and analysis of human melanoma and its precursors", Pigment Cell Res., 14, 2-8, 2001.
Lindsley, E. et al., "The hyperspectral imaging endoscope: a new tool for in vivo cancer detection", SPIE Proceedings, 5322, 75-82, 2004.
Chung, A. et al., "In vivo cytometry: a spectrum of possibilities", Cytometry Part A, 69A, 142-146, 2006.
Vo-Dinh, T. et. al., "Development of a multi-spectral imaging system for medical applications", Journal of Physics D: Appl. Phys. 36, 1663-1668, 2003.
Guillaud, M. et. al., "Nuclear Morphometry as a biomarker for bronchial intraepithelial neoplasia: Correlation with genetic damage and cancer development", Wiley-Liss, Inc., Cytometry Part A 63A: 34-40, 2005.
Qu, J. et. al., "Optical properties of normal and carcinomatous bronchial tissue", Applied Optics, vol. 33, No. 31, Nov. 1, 1994.
Schmitt, J. M. et. al., "Optical scattering properties of soft tissue: a discrete particle model", Applied Optics, vol. 37, No. 13, May 1, 1998.
Fawzy, Y. et. al., "Determination of scattering volume fraction and particle size distribution in the superficial layer of a turbid medium by using diffuse reflectance spectroscopy", Applied Optics, vol. 45, No. 16, Jun. 1, 2006.
Zeng, H. et. al., "Real-time endoscopic fluorescence imaging for early cancer detection in the gastrointestinal tract", Bioimaging 6, 151-165, 1998.
Palcic, B. et. al., "Detection and localization of early lung cancer by imaging techniques", Chest, 99: 742-43, 1991.
Lam, S. et. al., "Localization of bronchial intraepithelial neoplastic lesions by fluorescence bronchoscopy", Chest 113:696-702, 1998.
Gèelébart, B. et. al., "Phase function simulation in tissue phantoms: a fractal approach", Pure Appl. Opt. 5, 377-388, 1996.
Höckel, M. et. al., "Tumor hypoxia: definitions and current clinical, biological, and molecular aspects", Journal of the National Cancer Institute, vol. 93, No. 4, Feb. 21, 2001.
Fawzy, Y. et. al., "In vivo assessment and evaluation of lung tissue morphologic and physiological changes from non-contact endoscopic reflectance spectroscopy for improving lung cancer detection", Journal of Biomedical Optics, 044003-1, vol. 11(4), Jul./Aug. 2006.
Zeng, H. et. al., "Integrated endoscopy system for simultaneous imaging and spectroscopy for early lung cancer detection", Optics Letters, vol. 29, No. 6, Mar. 15, 2004.
Venugopalan, V. et. al., "Radiative transport in the diffusion approximation: An extension for highly absorbing media and small source-detector separations", Physical Review: E, vol. 58, No. 2, Aug. 1998.
Read, R. C., et. al., "Survival after conservative resection for T1 N0 M0 non-small cell lung cancer", Ann Thorac Surg, 49:391-400, 1990.
Lisenko, S.A., "Online quantitative analysis of multispectral images of human body tissues", Quantum Electronics 43 (8): 777-784 (2013).
Tomatis, S. et al., "Automated melanoma detection with a novel multispectral imaging system: results of a prospective study", Phys. Med. Biol. 50:1675-1687 (2005).

* cited by examiner

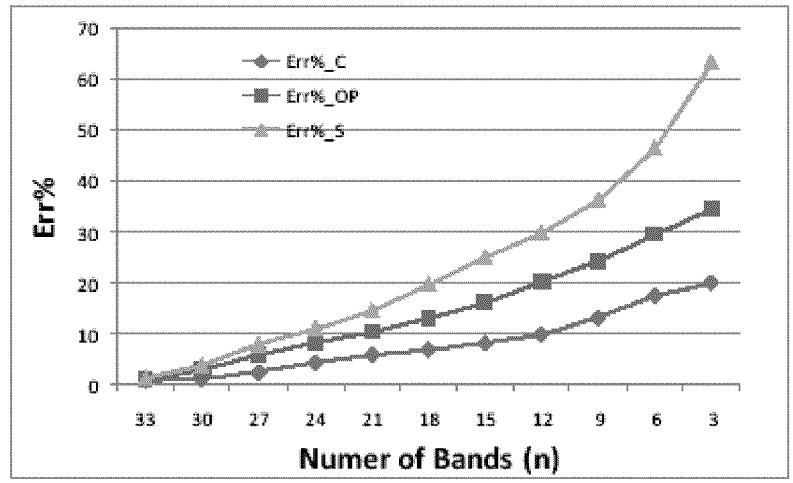
Figure 10: Accuracy comparison for the three approaches. (15 nm bandwidth)
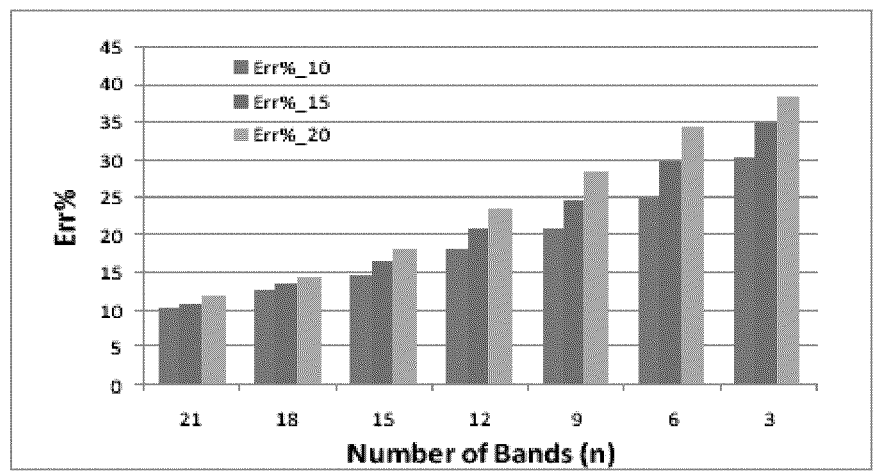
Figure 11: Effect of band width on the accuracy (optical property approach)

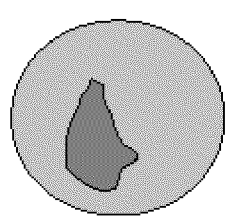 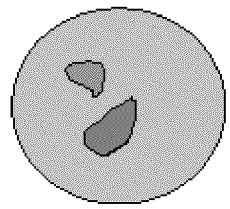
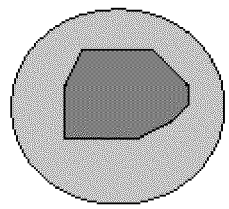 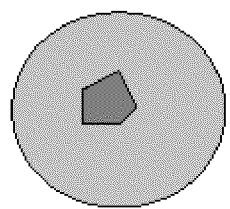
Oxygenated Haemoglobin Map    Deoxygenated Haemoglobin Map
Total Scattering Volume Fraction Map    Nucleus Volume Fraction Map
FIG. 15

RAPID MULTI-SPECTRAL IMAGING METHODS AND APPARATUS AND APPLICATIONS FOR CANCER DETECTION AND LOCALIZATION

This application claims priority from U.S. Provisional Patent Application No. 61/314,893, filed Mar. 17, 2010 which is hereby incorporated herein by reference.

BACKGROUND OF THE INVENTION

Field of the Invention

The present invention relates to methods and apparatus for multi-spectral imaging. The methods and apparatus may be applied, for example, in cancer detection and localization. Some embodiments can perform rapid multispectral imaging in the visible/NIR spectrum suitable for quantitative image-based determination of tissue physiological and morphological properties.

Background

Real-time monitoring and imaging of tissue physiological and morphological changes provides very useful information for diagnosis and therapy. For example, during endoscopic imaging such information could be of prime importance for detecting different pathologies, especially in the early stages, such as cancer and ischemia. Spectral images obtained during endoscopy could be used to derive information about tissue physiological and morphological properties. However, the variation in measurement geometry, the loss of absolute intensity measurements, light-tissue interaction complexity, and analysis computation costs make the measurement and quantification of true physiological and morphological properties difficult in terms of accuracy and processing time.

Conventional endoscopy uses white light reflectance images to view surface morphology and assess internal organs based on appearance such as, tissue color and surface morphology. While changes in physical appearance (e.g. color and morphology) are useful, in order to accomplish more reliable and earlier detection of cancer and other diseases, a number of research groups have investigated the use of tissue auto-fluorescence to improve the detection sensitivity of cancerous lesions. Unfortunately auto-fluorescence imaging improves detection sensitivity at the cost of reduced detection specificity. This can result in increased medical costs due to the enlarged number of biopsies as a result of an increased number of false positives. Increases in the frequency of biopsies also increase the morbidity to patients.

In order to achieve high diagnostic sensitivity and high specificity, some research has studied point spectroscopy modalities such as reflectance, fluorescence, and Raman spectroscopy, or "point" microscopic imaging modalities such as confocal microscopy, optical coherence tomography, and multi-photon excitation imaging, as additional techniques to be combined with white light and fluorescence imaging.

U.S. Pat. No. 6,898,458 to Zeng at al. discloses an apparatus and method for simultaneous imaging and non-contact point spectroscopy measurements in both the white light reflectance and fluorescence modes. The noncontact spectral measurement and imaging may be performed by placing a specially designed spectral attachment between the endoscope eyepiece and the camera. The image and the spectrum are simultaneously displayed on a monitor for observing by an operator.

United States Patent Application Publication 2009/0270702 to Fawzy et al. describes a method for analyzing reflectance spectra to obtain quantitative information about cancer-related changes such as micro-vascular blood volume fraction in tissue, tissue blood oxygen saturation (physiological parameters) as well as tissue scattering microparticle volume fraction and size distribution (morphological parameters). Both of the above references describe conducting spectral measurements though the eyepiece of a fiber endoscope. The spectral measurements involved point spectroscopy as opposed to spectral imaging.

Absorption characteristics and scattering characteristics of light differ according to the wavelength of the light. These differences are due to a distribution of different absorbent material such as blood vessels in the depth direction. Longer wavelengths of illumination light, such as infrared light, provide information from deeper parts of the tissue while shorter wavelengths of illumination light give information from the tissue near the surface. Detection of changes that occur near the tissue surface is essential for early cancer detection.

Several groups have reported intrinsic differences in optical absorption and scattering properties between malignant and benign lesions/normal tissues and have related these changes directly to tissue physiological and morphological changes that occur during cancer transformations. See M. P. L. Bard, A. Amelink, V. N. Hegt, W. J. Graveland, H. J. C. M. Sterenborg, H. C. Hoogsteden, J. G. J. V. Aerts, "*Measurement of Hypoxia-related parameters in bronchial mucosa by use of optical spectroscopy*", Am. J. Respir. Crit. Care Med., 171, 1178-1184, 2005; G. Zonios, L. T. Perelman, V. Backman, R. Manoharan, M. Fitzmaurice, J. Van Dam, and M. S. Feld, "*Diffuse reflectance spectroscopy of human adenomatous colon polyps in vivo*", Appl. Opt. 38, 6628-6636, 1998; B. Beauvoit, and B. Chance, "*Time-resolved spectroscopy of mitochondria, cells and tissue under normal and pathological conditions*", Mol Cell Biochem., 184, 445-455, 1998; J. R. Mourant, T. M. Johnson, and J. P. Freyer, "*Characterizing mammalian cells and cell phantoms by polarized backscattering fiber-optic measurement*", Appl. Opt. 40, 5114-5123, 2001; J. R. Mourant, A. H. Hielscher, A. A. Eick, T. M. Johnson, and J. P. Freyer, "*Evidence of intrinsic differences in the light scattering properties of tumorigenic and nontumorigenic cells*", Cancer, 84, 366-374, 1998; H. Zeng, C. MacAulay, B. Paclic, and D. I. McLeant, "*A computerized auto-fluorescence and diffuse reflectance spectroanalyser system for in vivo skin studies*", Phys. Med. Biol. 38, 231-240, 1993; R. J. Nordstorm, L. Burke, J. M. Niloff, and J. F. Myrtle, "*Identification of cervical intraepithelial neoplasia (CIN) using UV-excited fluorescence and diffuse-reflectance tissue spectroscopy*", Lasers Surg. Med. 29, 118-127, 2001; I. Georgakoudi, E. E. Sheets, M. G. Muller, V. Backman, C. P. Crum, K. Badizadegan, R. R. Dasari, and M. S. Feld, "*Trimodal spectroscopy for the detection and characterization of cervical precancers in vivo*", Am J Obstet Gynecol 186, 374-381, 2002; M. G. Muller, T. A. Valdez, I. Georgakoudi, V. Backman, C. Fuentes, S. Kabani, N. Layer, Z. Wang, C. W. Boone, R. R. Dasari, S. M. Shapshay, and M. S. Feld, "*Spectroscopic detection and evaluation of morphologic and biochemical changes in early human oral carcinoma*", Cancer 97, 1681-1692, 1997; M. P. L. Bard, A. Amelink, M. Skurichina, M. den Bakkerd, S. A. Burgers, J. P. van Meerbeeck, R. P. W. Duin, J. G. J. V. Aerts, H. C. Hoogsteden, and H. J. C. M. Sterenborg, "*Improving the specificity of fluorescence bronchoscopy for the analysis of neoplastic lesions of the bronchial tree by combination with

*optical spectroscopy: preliminary communication*", Lung Cancer 47, 41-47, 2005. The reflectance spectral measurements by all of these groups were conducted using a fiber optic probe inserted through the endoscope instrument channel. In addition the optic probe must be placed in contact with the tissue surface. These types of fiber optic probe measurement geometry are dramatically different from the imaging geometry (broad beam illumination and narrow spot detection).

Various groups have investigated multi-spectral or hyperspectral imaging for studying tissue pathology. For example, G. N. Stamatas, M. Southall and N. Kollias, *"In vivo monitoring of cutaneous edema using spectral imaging in the visible and near infrared"*, J. Invest. Dermatol. 126, 1753-1760, 2006; and G N. Stamatas, N. Kollias, *"Noninvasive quantitative documentation of cutaneous inflammation in vivo using spectral imaging"*, SPIE Proceedings 6078, 60780P, 2006, describe use of spectral imaging to obtain in vivo 2-D maps of various skin chromophores including oxy- and deoxy-hemoglobins. They use 18 narrow band filters to obtain images in the 400-970 nm range. A phase correction algorithm was then used to align the individual images at different wavebands to fight motion artifacts.

A state of the art endoscopic hyperspectral imaging system has been reported by the Farkas group. See U.S. Pat. No. 5,796,512 to Farkas et al.; D. L. Farkas and D. Becker, *"Applications of spectral imaging: detection and analysis of human melanoma and its precursors"*, Pigment Cell Res., 14, 2-8, 2001; E. Lindsley, E. S. Wachman and D. L. Farkas, *"The hyperspectral imaging endoscope: a new tool for in vivo cancer detection"*, SPIE Proceedings, 5322, 75-82, 2004; and A. Chung, S. Karlan, E. Lindsley, S. Wachsmann-Hogiu and D. L. Farkas, *"In vivo cytometry: a spectrum of possibilities"*, Cytometry Part A, 69A, 142-146, 2006. Their system acquires parallel and perpendicular polarized images at 32 evenly spaced bands from 380-690 nm in 0.25 seconds. A monochromator or AOTF (acousto-optic tunable filter) based tunable light source and a single high speed CCD camera was used for image acquisition. A 2.0 mm size catheter comprising an illumination fiber and two imaging fiber bundles was passed through the instrument channel to perform the hyperspectral imaging. This group used algorithms developed for fiber-probe point reflectance spectral analysis to analyze the imaging spectral data to derive a scatter size parameter image. In clinical tests, the system encountered problems from specular reflection interference and motion artifacts due to movement from either endoscope or patient.

Another system is disclosed in International Patent Application Publication WO2009/052607 to Fawzy which describes a method for quantifying tissue de-oxygenated blood index directly from images that are taken by illuminating the tissue with two different wavelength bands sequentially.

U.S. Pat. No. 7,729,751 to Ayame et. al. and United States Patent Application Publication 2009/0023991 to Gono et al. disclose methods to improve the visualization of the tissue color tone changes using the "electronic spectral imaging" technique (color correction techniques). "Electronic spectral imaging" is based on an estimation of reflectance spectra from RGB images or narrow band images using samples of the spectra which were measured a priori. "Electronic spectral imaging" does not provide accurate representations of true tissue reflectance properties and tissue physiology and morphology.

United States Patent Application Publication 2007/0024946 to Panasyuk et al. discloses a multispectral imaging system and method for real-time or near real-time assessment of tissue oxygen saturation, delivery and extraction during shock and resuscitation. In this system, spectral images are obtained by sequential illumination using different wavelengths.

There remains a need for cost-effective apparatus and methods for rapid multispectral imaging.

SUMMARY OF THE INVENTION

The invention has a number of aspects. Some of these may be applied independently as well as in combination with other aspects.

In one aspect, a multi-spectral imaging system is provided with parallel multi-band illumination and parallel multi-channel imaging detection to achieve video rate rapid multispectral imaging overcoming the motion artifacts. Specular reflection is automatically corrected by applying a data analysis algorithm.

Another aspect provides apparatus for multispectral imaging of an object. The object may, for example, comprise living tissue. The apparatus comprises a light source configurable to emit light having a first spectrum characterized by a first plurality of narrow bands. The apparatus is arranged to direct the light from the light source onto an area of the object. The apparatus comprises a multi-channel imaging light detector arranged to image the area of the object and configured to provide multi-channel image data. Image processing apparatus is configured to extract a plurality of spectral images from the image data. The plurality of spectral images comprise a spectral image corresponding to each of the plurality of narrow bands.

Another aspect, provides a system for multispectral imaging providing simultaneous images indicative of two or more of tissue blood volume, tissue oxygenation, tissue scatter volume and tissue scatter size parameter.

In one aspect, the present invention provides an apparatus for multispectral imaging of an object comprising a light source for illuminating the object, the light source being adapted to generate simultaneously illumination in at least two narrow wavelength bands, each of the narrow bands being within different wavelengths for producing spectral images in a visible/NIR range. A multichannel or multi-detector camera works in accordance with the simultaneous multi-band illumination to capture multiple images at these multiple wavelength bands simultaneously.

In one aspect, the present invention provides a light source that produces 18+ wavebands of illumination light and an image detecting device to capture corresponding 18+ spectral images at these wavebands. In some embodiments the light source is configured to produce 12 to 52 narrow wavelength bands. The obtained spectral images are processed and analysed to produce absorption and scattering spectral images. An intensity calibration algorithm uses measured reflectance spectra from a pixel of an image and in-vitro optical absorption coefficients to correct for intensity of the spectral images from a light coupling variation/error between a light source, a tissue (subject being imaged), and the image detecting device.

In another aspect, the present invention provides a method for quantification of tissue physiological and morphological information comprising the steps of illuminating an object simultaneously with light in at least two narrow bands, simultaneously acquiring multiple images corresponding to these wavelength bands, each of the narrow bands being within different wavelengths for producing spectral images in a visible/NIR range, producing a plurality of spectral images, correcting an intensity of the spectral images using measured reflectance spectra from a pixel of the image and in-vitro optical absorption coefficients, producing separately absorption and scattering spectral images along a full spectral range, and quantifying at least one physiological parameter and/or at least one morphological parameter from the obtained absorption and scattering images.

In yet another aspect, the present invention provides an apparatus for non-invasive rapid multi-spectral imaging for cancer detection and localization by an endoscopy system.

In another aspect, the present invention provides a system for non-invasive rapid multi-spectral imaging for cancer detection by an optical probe.

In one aspect, the present invention provides a programmable multifunctional system which can perform white light reflectance imaging, fluorescence imaging and multi-spectral reflectance imaging.

Some embodiments apply image detectors having three imaging channels. The imaging detectors are commercially available color cameras in some embodiments.

In yet another aspect, the present invention provides an image detector with four imaging channels. Correspondingly, the light source is programmed to generate 4 narrow bands of illumination simultaneously. Each of the narrow bands is within the B, G, R, and NIR bands respectively and they shift simultaneously with time to different wavelength sets.

In some embodiments the light source comprises a programmable light source, such as a digital micromirror device.

In some embodiments, the light source comprises a filter wheel based light source which provides simultaneous multiple narrow band illumination.

In other embodiments, an acousto-optic tunable filter is used with a fiber laser based supercontinuum light source or a laser-driven light source for producing multiple narrow band illumination profiles.

In some embodiments white light images are synthesized from spectral images.

In another aspect of the present invention, a modeling approach is used to determine optimized wavelength bands for rapid multi-spectral imaging.

In yet another aspect, the present invention provides a real-time imaging of tissue blood volume distribution, tissue oxygenation, tissue scatter volume distribution and scatter size parameter spatial distribution.

In one aspect of the present invention, multi-spectral images are captured by an image detector located at a tip of an endoscope. The image detector is coated with a special pattern of filters to facilitate at least three and preferably four channel imaging (B, G, R, NIR).

In one aspect of the present invention, multi-spectral images are captured by a color camera having three (R, G, B) channels with spectral overlaps. For example, the camera may have a CCD, CMOS or APS light sensor comprising a pattern of filter elements which pass light in different overlapping bands. For example, the filter elements may be arranged in a Bayer mosaic pattern.

In yet another aspect of the present invention, a calibration method is used to decompose images from a standard color camera (such as a commercial camera) to provide narrow-band images.

In some embodiments, a light source for producing a plurality of illumination profiles comprises a plurality of solid-state light emitters such as LEDs located at a tip of an endoscope.

In yet another aspect, the present invention provides a method for optimizing wavelength bands for spectral imaging. According to one aspect, the optimizing method is based on an optimized light transport model.

Another aspect provides apparatus and methods for rapid multispectral imaging in which spectral images are generated from a plurality of simultaneous narrow band images. In some embodiments apparatus and method obtains a plurality of spectral images simultaneously in video rate real time. The images may indicate physiological properties such as, e.g. tissue blood volume, tissue oxygenation, tissue scatter volume and tissue scatter size parameters. In some embodiments the apparatus and methods additionally obtain white light and/or fluorescence images.

Act provides a multi-spectral imaging method. The method comprises exposing an area of an object to light having a spectrum comprising a plurality of narrow wavelength bands, acquiring image data comprising an image of the exposed object using a multi-channel imaging detector, and extracting a plurality of spectral images from the image data, the plurality of spectral images comprising a spectral image corresponding to each of the plurality of narrow bands.

Another aspect provides a multi-spectral imaging method comprising exposing an area of an object to light in N narrow wavelength bands and obtaining images of the object while it is exposed to the light. The exposing is performed in a sequence of steps. Each step comprises simultaneously exposing the object to light having a spectrum consisting essentially of a set of n of the N narrow wavelength bands at a time and obtaining an image of the object using a multi-channel imaging detector. The method includes processing multi-channel image data from the multi-channel imaging detector to obtain spectral images corresponding to the N narrow wavelength bands. The processing may comprise multiplying vectors of pixel values by a calibration matrix.

In addition to the exemplary aspects and embodiments described above, further aspects and embodiments will become apparent by reference to the drawings and study of the following detailed description.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 10 is a graph showing an accuracy of three approaches of an optimization procedure of the present invention;

FIG. 11 is a graph showing the effect of band width on the accuracy of an optimization procedure of the present invention;

FIG. 15 is an illustration of resultant images such as may be obtained with an embodiment of a method and apparatus of the present invention.

DETAILED DESCRIPTION

The figures and the following descriptions depict specific example embodiments. Those skilled in the art would appreciate that the features described below may be combined in other various ways to form multiple variations of the invention.

A multi-spectral imaging system provides parallel multi-band illumination and parallel multi-channel imaging detection to achieve high rate multi-spectral imaging. The imaging rate may be high enough to avoid motion artifacts. In some embodiments imaging is performed at video rates (e.g. 24 frames per second or more). Specular reflection may be automatically corrected for by a data analysis algorithm as described below.

Methods and apparatus for correcting the recorded image intensity to compensate for the effect of measurement geometry variations are also described below. Such methods and apparatus may be used in combination with a multi-spectral imaging system or in other applications. The methods and apparatus may be employed, for example, in generating video rate or near video rate quantified images of the physical, physiological, and morphological properties of tissue. For example, such methods and apparatus may be provided in a system that provides images indicating one or more of: tissue blood volume, tissue oxygenation, tissue scatter volume and tissue scatter size parameter. White light and/or fluorescence images may also be provided.

Some embodiments provide a programmable multifunctional endoscopy system that can perform white light reflectance imaging (WLR), fluorescence imaging (FL) and multi-spectral reflectance imaging.

Figure 1:
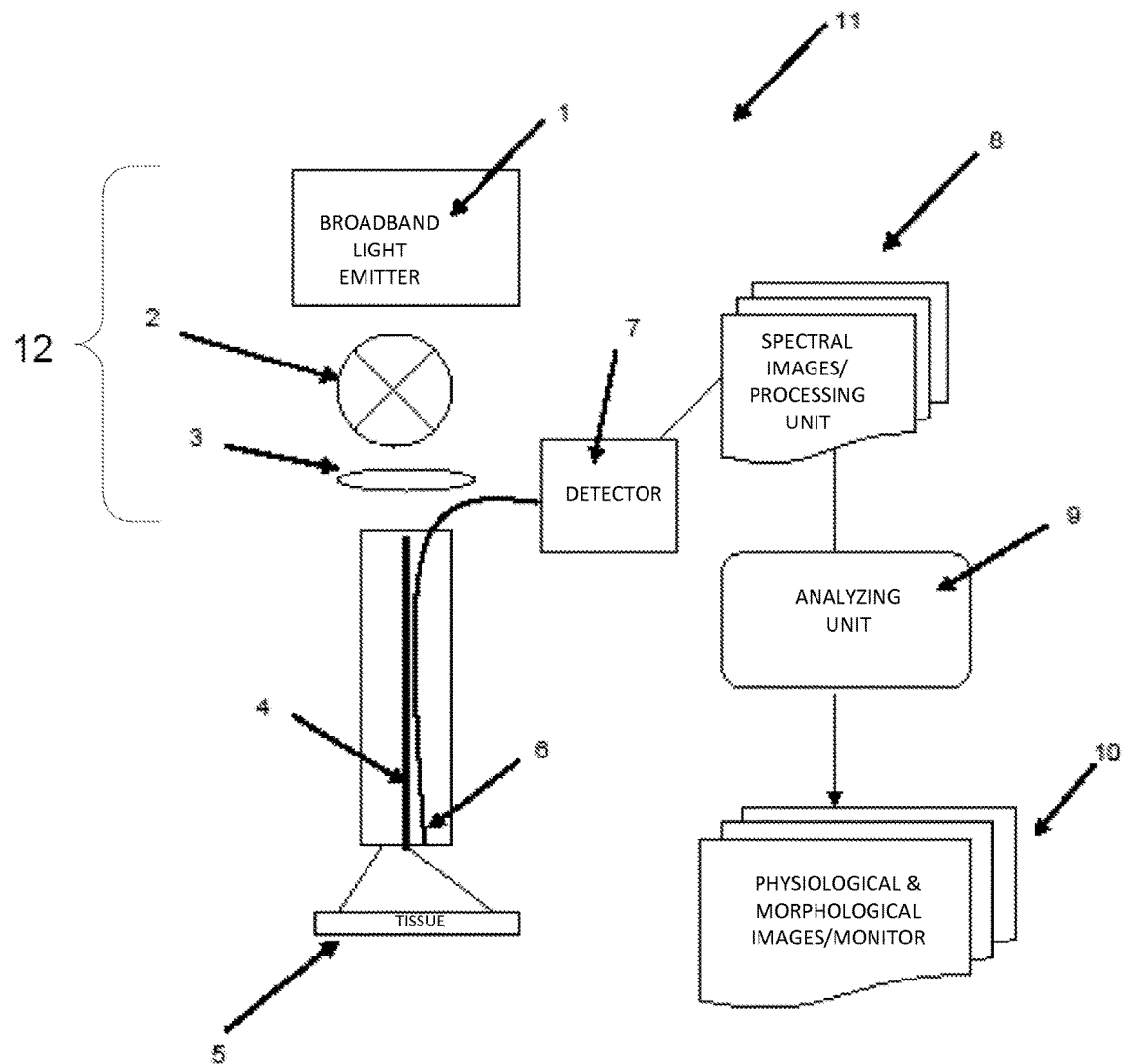
FIG. 1 is a schematic illustration of an endoscopy system according to an embodiment of the present invention.

FIG. 1 is a block diagram showing functional elements of a programmable multifunctional endoscopy system 11. System 11 comprises a light source 12 for generating illumination light comprising light in a plurality of narrow spectral bands and an optical camera/detector 7 for acquiring and generating spectral images corresponding to the spectral bands. The light emitted by light source 12 may consist essentially of light in the plurality of spectral bands. In some embodiments, at least 50% or at least 80% of the light energy in the illumination light emitted by light source 12 is in the plurality of spectral bands. In the illustrated embodiment, light source 12 comprises a broadband light emitter 1 and an illumination light filter 2 for generating plurality of narrow spectral bands. Light filter 2 may, for example, comprise a filter on a rotating filter wheel. Light emitter 1 may comprise, for example, a Xenon lamp which provides broad spectral illumination light in the wavelength range of 400-800 nm.

In an alternative embodiment, light source 12 comprises a plurality of narrow-band light sources that each emit light in one of the plurality of spectral bands. For example, light source 12 may comprise a plurality of light-emitting semiconductor devices (such as, for example light-emitting diodes LEDs).

In some embodiments, light source 12 is adapted to permit the spectral make up of the illumination light to be changed. For example, during a first period, light source 12 may emit light in a first set of narrow spectral bands, during a second period the light source 12 may emit light in a second set of narrow spectral bands different from the first set. This may be continued for a number of periods.

In some embodiments, light source 12 is configured to repeatedly cycle through a plurality of periods and, in each period, to emit illumination light in a plurality of spectral bands such that the spectrum of the illumination light (e.g. the specific spectral bands which make up the illumination light in that period) changes from period-to period.

The illumination light emitted by light source 1 passes through filter 2 which filters out light that is outside of the plurality of narrow spectral bands to leave illumination light that is concentrated in the plurality of narrow spectral bands. Such illumination light is focused by a lens 3 into an illumination light guide 4 to irradiate a tissue 5 (an object being imaged). Light reflected by the tissue is captured by an imaging means which, in this example, comprises a collecting lens (not shown), an imaging light guide 6 and a detector 7. Detector 7 may simultaneously acquire image data for each of the plurality of narrow spectral bands. This facilitates rapid acquisition of multi-spectral images.

Detector 7 may comprise, for example, three charge-coupled devices (CCDs) such as a blue CCD responsive to light having wavelengths of 400-500 nm, a green CCD responsive to light having wavelengths in the range of 500-600 nm, and a red/NIR CCD responsive to light having wavelengths in the range of 600-800 nm. Detector 7 may further comprise a plurality of dichroic mirrors. In one example of such an embodiment, a light beam from image guide 6 enters detector 7 and impinges onto a first dichroic mirror which reflects light having wavelengths smaller than 500 nm toward the blue CCD while transmitting light having wavelengths >500 nm. A second dichroic mirror reflects light having wavelengths smaller than 600 nm toward the green CCD and transmits light having wavelengths >600 nm toward the red/NIR CCD.

Optionally, detector 7 may comprise band pass filters in optical paths upstream from the CCDs (for example, one bandpass filter may be disposed in close proximity in front of each of the CCDs to further optically process the incident light. The CCDs may have exposure times shorter than video rate to accommodate fast image acquisition for multi-spectral imaging.

Images obtained by the CCDs are processed by a processing unit 8 into plurality of spectral images. The obtained spectral images are then analyzed by the analyzing unit 9 and the resulted physiological and morphological images of the tissue are displayed on a desired output means such as a monitor 10. Analyzing unit 9 may, for example, apply a modeling algorithm as described below.

Light source 12 may provide visible and/or near infrared (NIR) radiation. For example, light source 12 may provide illumination light in the visible/NIR band extending from about 400 nm to at least about 800 nm.

In some embodiments, light source 12 has a mode of operation in which it emits broadband illumination in at least the visible range. Such a mode may be useful for generating images to guide an operator during an endoscopy procedure. With light source 12 operating to emit broadband visible radiation, detector 7 may capture an image that is similar to a conventional RGB image with the exception that the red channel covers e.g. 600-800 nm instead of a narrower range such as 600-700 nm. As noted above, light source 12 can provide simultaneous multiple narrow band (NB) illumination (e.g. at 405 nm, 505 nm, and 605 nm). Advantageously, light source 12 can be quickly tuned to issue illumination light having a spectrum made up of the next multi-NB set (e.g. 420 nm, 520 nm, and 635 nm). In some embodiments, each multi-NB set has the same number of narrow band components as detector 7 has channels. For example, for a detector 7 as described above having three channels each multi-NB set may comprise three narrow bands.

Figure 2:
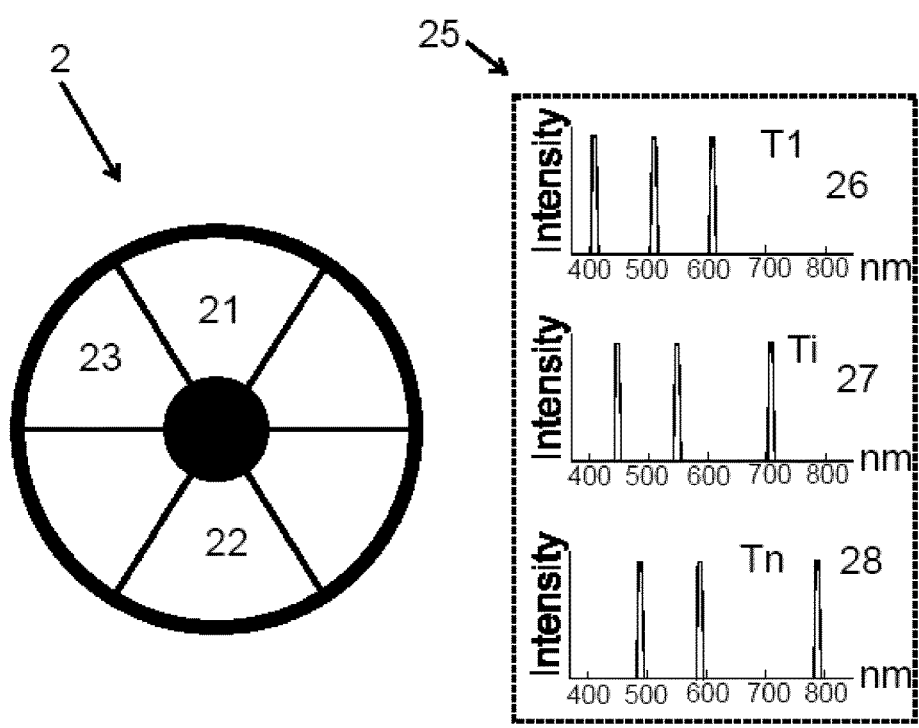
FIG. 2 is a schematic illustration of a rotating filter wheel useful for generating simultaneous illumination in multiple narrow-bands of different spectral profiles at different times.

As illustrated in FIG. 2, filter wheel 2 may be used to generate illumination light in a sequence of periods such that in different periods the illumination light has a spectral make up that comprises different sets of three narrow bands. Filter wheel 2 may include more than one filter. When each of these filters is in the optical path between light emitter 1 and the object being imaged, the illumination light is made essentially of three narrow bands that are delivered simultaneously to the object. The bands may, for example, comprise one band in the blue part of the spectrum, one band in the green part of the spectrum and one band in the red or infrared part of the spectrum. For example, filter 21 may generate illumination spectrum 26 during time period T1; filter 22 generates illumination spectrum 27 during time period Ti; and filter 23 generates illumination spectrum 28 during time period Tn. In some implementations, the individual filters in filter wheel 2 can generate simultaneously more or fewer than three narrow wavebands.

In some embodiments the filter wheel includes filters that provide a total of 12 to 52 different bands of illumination light with each filter providing two or three different bands. The number of narrow passbands for each filter is equal to or less than the number of channels provided by the detector in some embodiments.

In one example embodiment, filter wheel 2 includes six filters providing a total of 18 bands of illumination light, three bands at a time. In an example embodiment each filter provides a different spectral illumination profile comprised of a different set of three narrow bands of light. A table below shows one example of possible wavelengths of the 18 selected bands. In some embodiments the narrow bands have bandwidths of 20 nm or less. The 10 nm columns represent wavelength selections optimized for narrow bands having bandwidths of 10 nm. The 15 nm columns are wavelength selections optimized for the case where the narrow bands have bandwidths of 15 nm. The wavelengths of the narrow bands may be evenly or unevenly spaced apart.

| Filter No. | Blue Band | | Green Band | | Red Band | |
| --- | --- | --- | --- | --- | --- | --- |
|  | 10 nm | 15 nm | 10 nm | 15 nm | 10 nm | 15 nm |
| 1 | 415 | 415 | 515 | 510 | 610 | 615 |
| 2 | 435 | 435 | 525 | 525 | 625 | 625 |
| 3 | 450 | 445 | 540 | 545 | 640 | 645 |
| 4 | 465 | 460 | 560 | 560 | 665 | 665 |
| 5 | 475 | 475 | 575 | 575 | 690 | 690 |
| 6 | 490 | 490 | 590 | 595 | 760 | 760 |

For example, a first filter may provide simultaneously a light in a blue band (415 nm), green band (510 nm or 515 nm) and red band (610 nm or 615 nm). A second filter may provide illumination profile of 435 nm, 525 nm and 625 nm; a third filter may provide 445 nm or 450 nm, 540 nm or 545 nm and 640 nm or 645 nm; a forth filter may provide 460 nm or 465 nm, 560 nm and 665 nm; a fifth filter may provide 475 nm, 575 nm and 690 nm; and a sixth filter may provide 490 nm, 590 nm or 595 nm and 760 nm illumination light.

Figure 2A:
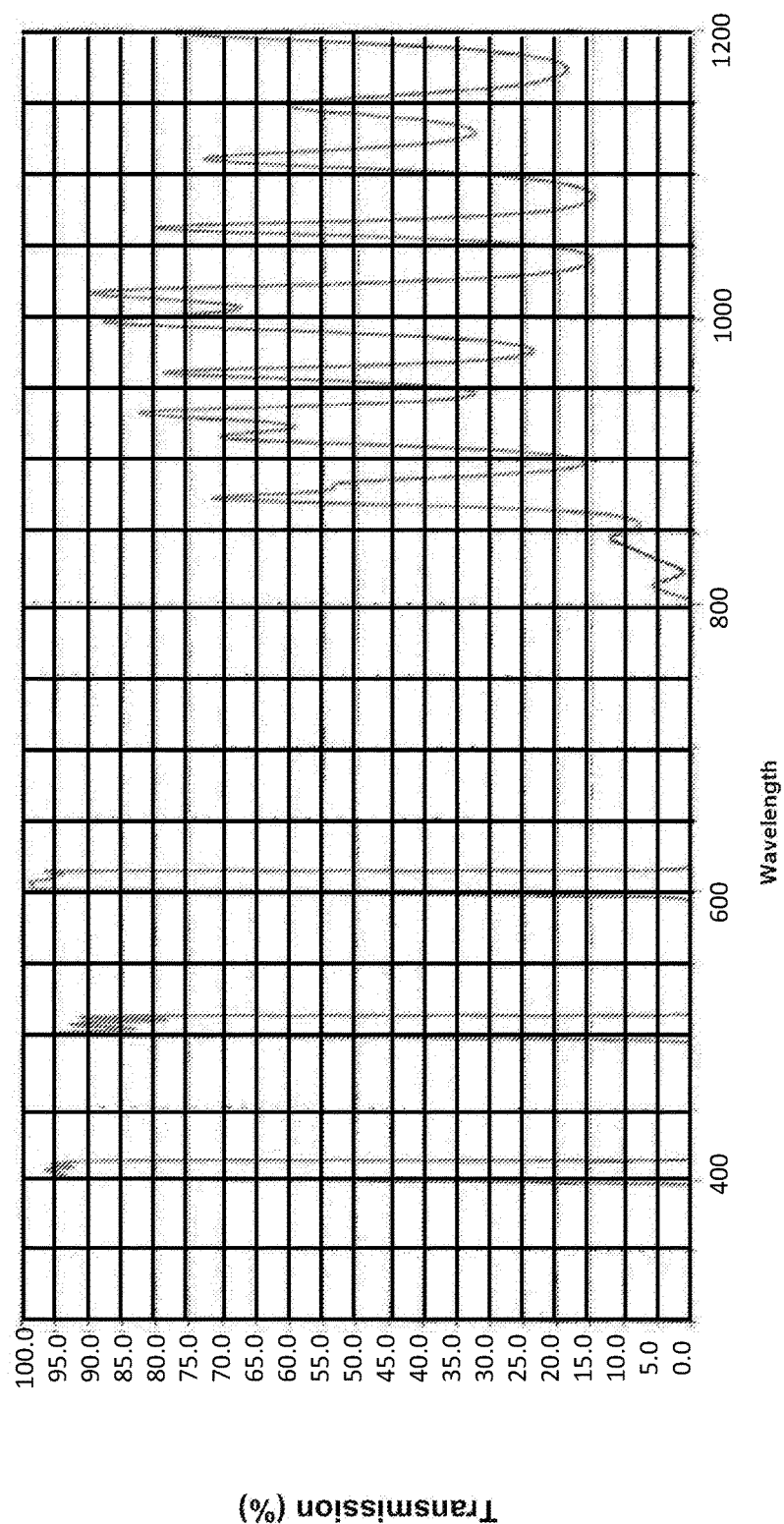
FIG. 2a is a graph illustrating spectral properties of a custom-made filter passing multiple wavelength bands of light.

An example transmission characteristic of a custom-made filter on filter wheel 2 is shown in FIG. 2a. As shown this particular filter on the filter wheel 2 can pass simultaneously multiple bands of light in different wavelengths. In addition, a short wave pass filter can be used to remove the transmitted light above 800 nm.

With a filter wheel 2, switching between different spectral profiles is achieved by rotating the filter wheel 2. In some embodiments, the filter wheel 2 is rotated at a speed of about 30 r/s. Light from light emitter 1 may be used without narrow band filtering to provide white light illumination (e.g. 400-700 nm) for use in white light reflectance imaging. This may be achieved by providing one or more segments of filter wheel 2 which do not have narrow-band filters and/or providing a selectable optical path that bypasses filter wheel 2.

The light source 12 shown in FIG. 1 is only one example from among a large number of suitable light sources that may be applied for generating illumination having a spectrum comprising a plurality of narrow bands that can be imaged in the same exposure of detector 7. In one alternative example embodiment, an acousto-optic tunable filter (AOTF) based light source or a liquid crystal tunable filter (LCTF) based light source is used. In another example embodiment a digital micromirror device (DMD) based spectrally programmable light source is used for providing effectively simultaneous multiple NB illumination. Some commercially-available DMD-based light sources are capable of switching among up to 7000 spectra per second It is likely that this number will increase with continuing development of DMD-based light sources.

In another alternative example embodiment, a light source comprises one or more acousto-optic tunable filters (AOTFs) for essentially simultaneous generation of multiple NB illumination. For example, a model SC450-AOTF light source from Fianium, UK, can generate light in which the spectrum has up to eight NB components. The AOTF can be used with a fiber laser based supercontinuum light source.

In another example embodiment, light source 12 comprises a plurality of separate light emitters which each emit narrow band light in one or more specific wavelength bands. The light emitters may comprise light-emitting semiconductor devices such as light-emitting diodes (LEDs) for example. In some embodiments the light source comprises LEDs of several types with a plurality of LEDs of each type.

In some embodiments a light source 12 is located at a distal end of an endoscope. For example, a plurality of LEDs or LDs may be located at the distal end of the endoscope. This arrangement does not require a light guide 4 for carrying illumination light. The plurality of LEDs may be electronically switched at high rates to provide a plurality of illumination segments with specific spectral properties. The LEDs can be switched on and off electrically to conveniently achieve simultaneous multi-band illumination and be synchronized with the camera for corresponding image acquisition. The many LEDs may be arranged in a circle to achieve uniform illumination light at the tissue surface.

Figure 3:
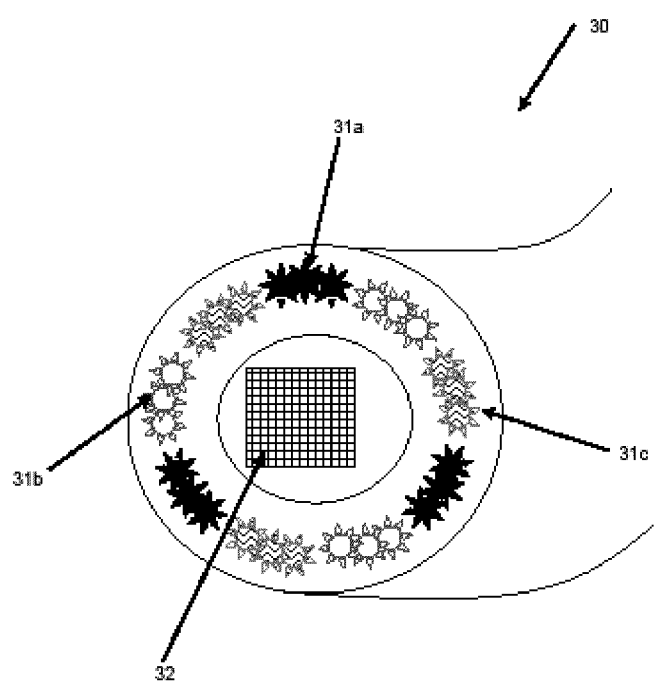
FIG. 3 is a schematic illustration of a light source located at a distal end of an endoscope.

FIG. 3 shows a distal end 30 of an endoscopy system with a plurality of LEDs 31 to generate light in a plurality of desired wavelength bands. The LEDs 31 may be mounted at the distal end of the endoscope surrounding a lens 32, which can form an image at the imaging light guide 6 that in turn carries the image to detector 7. Alternatively, a miniature camera 7 may be placed directly behind lens 32, eliminating the need of imaging light guide 6. This later set-up can also be used for open-field imaging applications, such as imaging of the human skin.

A bandpass filter may optionally be deposited on the light-emitting face of each LED to help narrow down the spectral bandwidth to the desired specifications. In the embodiment illustrated in FIG. 3, the set of three LEDs 31a may provide illumination light in three corresponding narrow bands ($b_a$, $g_a$, $r_a$), the LEDs 31b may provide illumination light in three corresponding narrow bands ($b_b$, $g_b$, $r_b$) at the same or different wavelength of LEDs 31a, and LEDs 31c may provide light in three narrow bands ($b_e$, $g_e$, $r_e$) at the same or different wavelength of LEDs 31a and/or 31b.

Figure 4:
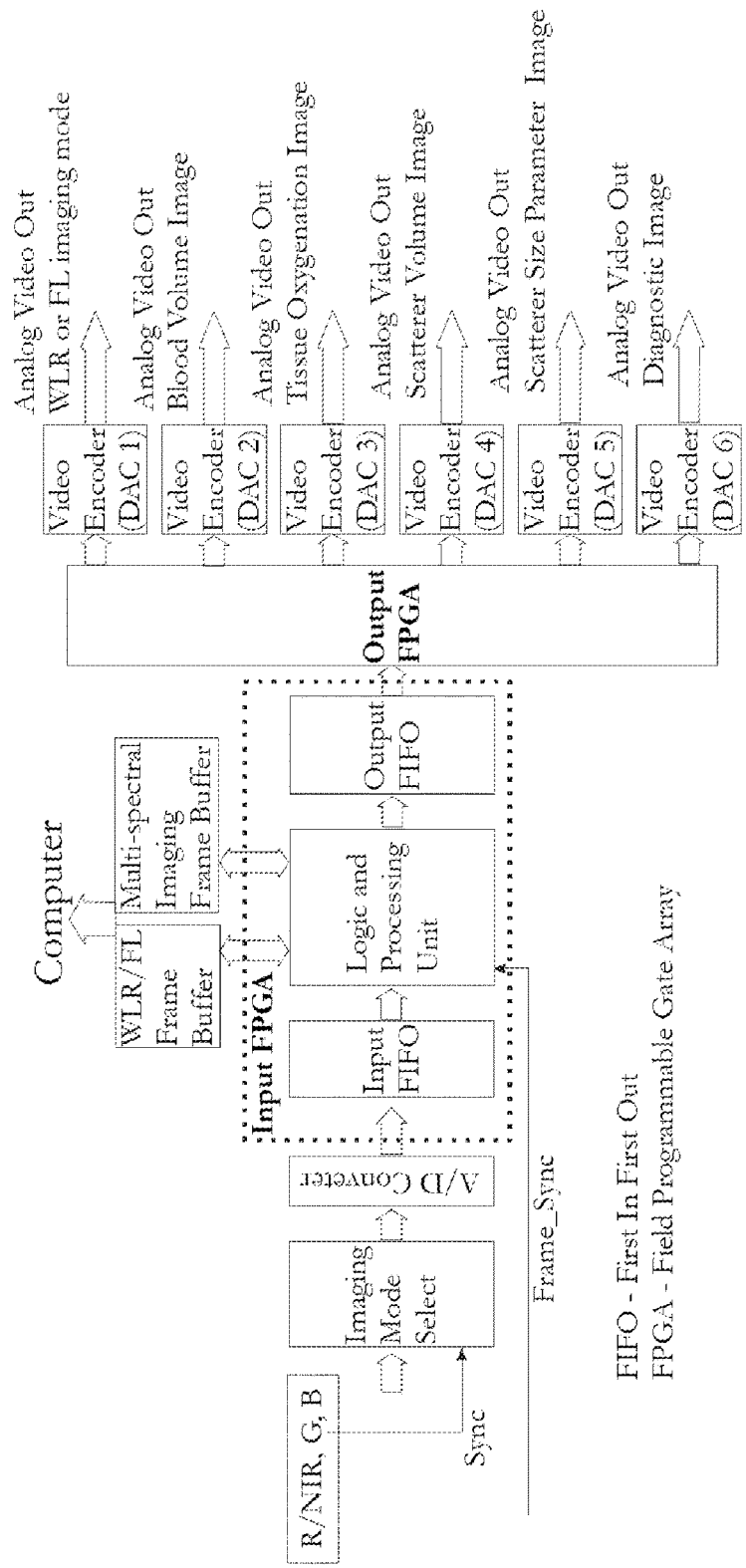
FIG. 4 is a block diagram of example programmable image acquisition and processing electronics.

FIG. 4 shows details of example image acquisition and processing electronics 8. First image modes are selected and then the imaging signals are digitized by an A/D converter and sent to an Input FPGA (field programmable gate array) for processing. Inside the Input FPGA, the digitized images are directed to an Input FIFO (first in first out) image buffer and then into a Programmable Logic and Processing Unit which can direct the images into either a WLR/FL (white light reflection/fluorescence) Frame buffer or a multi-spectral imaging buffer for further processing. The WLR images and the FL images may share the same buffer because these two imaging modalities are typically not performed simultaneously. A separate buffer with much larger memory is designated for multi-spectral imaging. The employment of two buffers also facilitates simultaneous WLR imaging and multi-spectral imaging if the light source is programmed to output the multi-NB illumination series and the WRL illumination in the same cycle. Various image processing functions may be implemented within the Input FPGA such as alignment of the three images taken by the red/near infrared (R/NIR), green (G) and blue (B) CCDs.

An algorithm developed to execute the modeling technique described herein below is used for processing the multi-spectral images to derive a reflectance spectrum for each pixel which is then analyzed to obtain tissue physiological and morphological parameters for each pixel producing at least four images, such as, e.g., tissue blood volume image, tissue oxygenation image, tissue scatter volume image, and tissue scatter size parameter image. In another embodiment, additional images, such as, e.g., an oxyhemoglobin image, a deoxyhemoglobin image, a tissue water volume image and/or an image of other chromophore distributions can be produced. Based on these images, a tissue diagnostic image may be generated that classifies each pixel as benign/normal or malignant.

Various different algorithms of performing a number of analyses can be incorporated by programming them into the FPGA. The processed digital images are output by an Output FIFO to an Output FPGA which exports various images into different Video Encoders (DACs) to transform the digital image signals into standard analog videos to be displayed on standard analog monitors. The two image frame buffers can be connected to a PC computer, so that at any stage of the above mentioned process the digital images can be transferred into the PC for further processing and analyses and displaying the results on the computer monitors. The PC can be equipped with a GPU (Graphics Processing Unit) video processing card to speed up the image processing and data analysis.

In an alternative embodiment, detector 7 has four imaging CCDs such as B (400-500 nm), G (500-600 nm), R (600-700 nm), and NIR (700-800 nm). In such embodiments, light source 12 may be adapted to generate illumination light in which the spectrum is made up of four narrow bands of light. The narrow bands may be within the B, G, R, and NIR bands respectively. The pass wavelength for the narrow bands may be controlled to change with time. This permits faster multi-spectral imaging to be performed.

In another embodiment, a white light reflectance image is synthesized from the acquired narrow-band spectral images. For each pixel, a reflectance spectrum can be generated so that a RGB color for the pixel can be obtained by multiplying the reflectance spectrum by an CIE (International Commission on Illumination) standard illumination spectrum to generate the radiance spectrum and convoluting the radiance spectrum with eye cone sensitivity spectra to generate the final R, G, B color quantities for display on a monitor for observing by the operator.

In an alternative embodiment a video endoscope has a detector (e.g. a CCD) installed at the tip of the endoscope. In such embodiments an image light guide 6 is not required. The detector chip is coated with a I pattern of filters to facilitate three- or four channel imaging (B, G, R, NIR). A possible pattern is illustrated in the following table.

| B | G | B | G | B | G |
|---|---|---|---|---|---|
| R | NIR | R | NIR | R | NIR |
| B | G | B | G | B | G |
| R | NIR | R | NIR | R | NIR |

Figure 5:
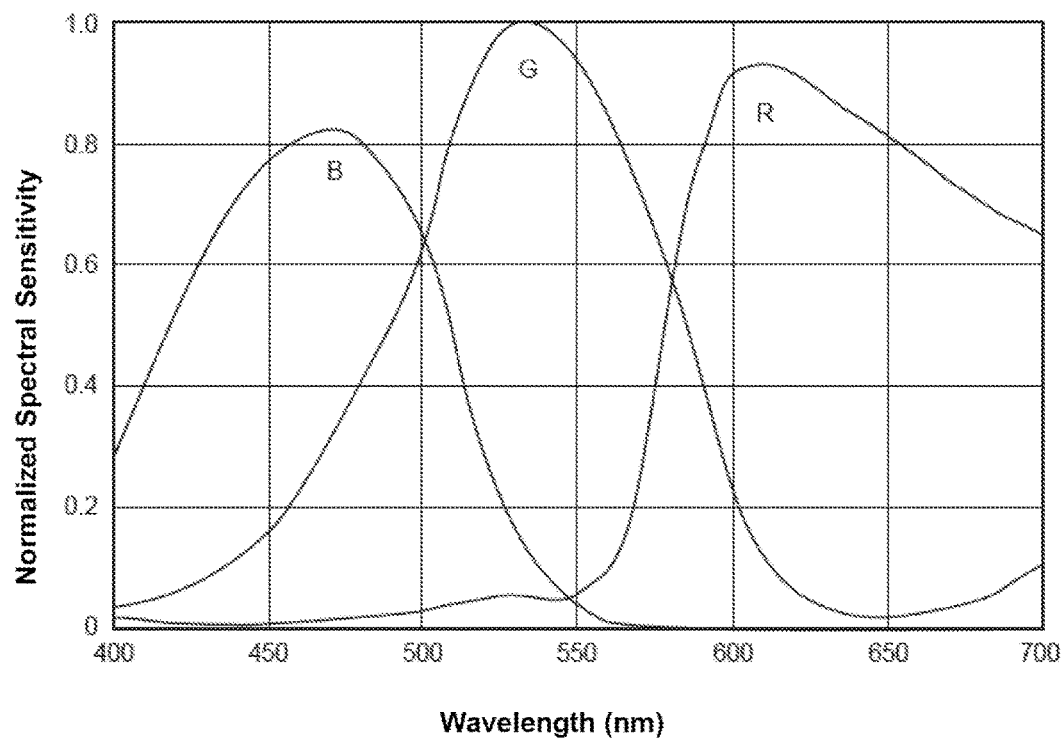
FIG. 5 is a graph illustrating overlapping spectral responses for a three (red (R), green (G) and blue (B)) channels of a CCD.
Figure 6:
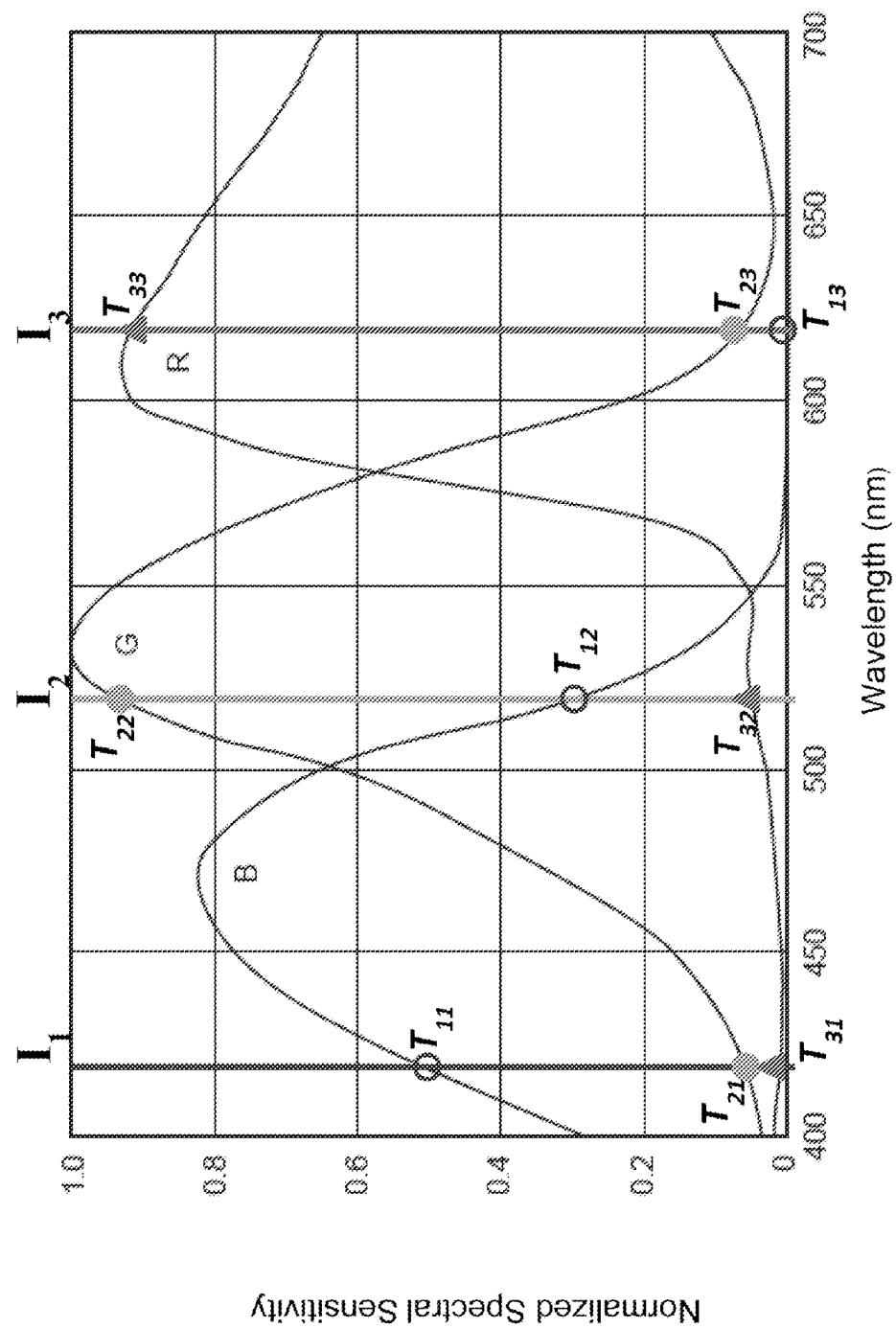
FIG. 6 is a graph illustrating CCD output readings in response to three wavelengths due to their overlapping spectral responses.

In another embodiment, a commercial color imaging detector (e.g. CCD, CMOS or APS detector) may be used as a detector. The detector may have filters applied in a Bayer filter mosaic to obtain R, G, B images. The filters in many commercially available imaging detectors can have spectral responses that overlap with one another f FIG. 5 shows example filter characteristics for filters of an example CCD image detector. The advantage of using this type of detector is reduced cost.

Where the filter characteristics overlap, a calibration procedure may be performed to obtain accurate reflectance signals corresponding to the individual narrow band illumination wavelengths. As illustrated in FIG. 6, under the simultaneous illumination of three wavelengths seated in the B, G, R spectral bands, CCD output readings for each of the three image channels will have contributions from all the three wavelengths due to their overlapping spectral responses. Assuming that the light intensities that reach the CCD are $I_1$, $I_2$, and $I_3$ for the blue, green, and red narrow-band wavelengths respectively, the CCD blue channel reading can have contributions from the blue light as determined by the sensitivity $T_{11}$, from the green light as determined by the sensitivity $T_{12}$, and from the red light as determined by the sensitivity $T_{13}$. The CCD blue channel reading $C_1$ equals:

$$C_1 = T_{11}I_1 + T_{12}I_2 + T_{13}I_3 \tag{1}$$

Similarly the CCD green channel reading $C_2$ and red channel reading $C_3$ are given as follows:

$$C_2 = T_{21}I_1 + T_{22}I_2 + T_{23}I_3 \tag{2}$$

$$C_3 = T_{31}I_1 + T_{32}I_2 + T_{33}I_3 \tag{3}$$

These three equations can be expressed in a matrix format as follows:

$$\begin{bmatrix} C_1 \\ C_2 \\ C_3 \end{bmatrix} = \begin{bmatrix} T_{11} & T_{12} & T_{13} \\ T_{21} & T_{22} & T_{23} \\ T_{31} & T_{32} & T_{33} \end{bmatrix} \begin{bmatrix} I_1 \\ I_2 \\ I_3 \end{bmatrix} \tag{4}$$

A T matrix as illustrated in Equation (4) may be determined by performing a calibration. Calibration may be performed by illuminating the CCD with light $I_1$, $I_2$, and $I_3$ in separate exposures.

When the CCD is illuminated only by $I_1$ (with $I_2 = I_3 = 0$), we have:

$$C_1 = T_{11}I_1 T_{11} = C_1/I_1$$

$$C_2 = T_{21}I_1, \text{ i.e. } T_{21} = C_2/I_1$$

$$C_3 = T_{31}I_1 T_{31} = C_3/I_1$$

$I_1$ can be measured by an optical power meter, while C1, C2, and C3 are readings from the CCD's B, G, R channels respectively. Similarly when illuminated by $I_2$ only ($I_1 = I_3 = 0$), we get $$T_{12} = C_1/I_2$$

$$T_{22} = C_2/I_2$$

$$T_{32} = C_3/I_2$$

When illuminated by $I_3$ only ($I_1 = I_2 = 0$), we get $$T_{13} = C_1/I_3$$

$$T_{23} = C_2/I_3$$

$$T_{33} = C_3/I_3$$

The calibration matrix $$T = \begin{bmatrix} T_{11} & T_{12} & T_{13} \\ T_{21} & T_{22} & T_{23} \\ T_{31} & T_{32} & T_{33} \end{bmatrix}$$

is a square matrix. By inverting the calibration matrix T, we can obtain the calibrated light intensity from the CCD readings:

$$\begin{bmatrix} I_1 \\ I_2 \\ I_3 \end{bmatrix} = \begin{bmatrix} T_{11} & T_{12} & T_{13} \\ T_{21} & T_{22} & T_{23} \\ T_{31} & T_{32} & T_{33} \end{bmatrix} \begin{bmatrix} C_1 \\ C_2 \\ C_3 \end{bmatrix} \tag{5}$$

When a different illumination set of $I_1$, $I_2$, $I_3$ (at different wavelengths) are used the calibration needs to be repeated for the new wavelengths set. If six different triple narrow band (NB) sets are used in the spectral imaging system, six sets of calibrations need to be carried out.

In an alternate embodiment, snap-shot multi-spectral images of suspicious areas (which may be found, for example, by WLR imaging and/or FL imaging) can be captured for off-line analysis (or online but not fast enough to display the results in video rate) to derive snap-shot physiological and morphological images for diagnosis.

Figure 7:
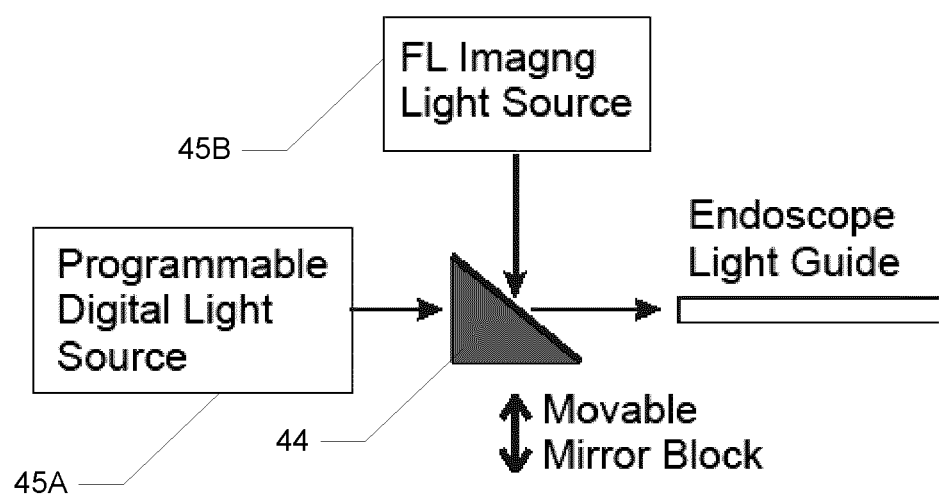
FIG. 7 is a schematic illustration of a light source according to another which combines a fluorescence light source for providing illumination for fluorescence imaging and a programmable digital light source for providing illumination for white light reflectance and multi-spectral imaging.

FL imaging illumination may be generated by a light source as shown in FIG. 7. The FL imaging light source can provide illumination for FL imaging, while a programmable digital light source or a combination of a light emitter with a set of interchangeable filters (such as filters on a filter wheel) can provide illumination for WLR imaging and multi-spectral imaging. In the embodiment of FIG. 7, when the mirror block 44 is in the position as shown in the figure, light from the programmable digital light source 45A is blocked, while light from the FL imaging light source 45B is reflected to the endoscope light guide. When mirror block 44 is moved away, light from the programmable digital light source 45a is directed to the endoscope light guide. Mirror block 44 may be moved by a solenoid or other actuator under computer control.

In some embodiments both the light source and the image acquisition and processing electronics are fully programmable. In such embodiments, various ways of acquiring multi-spectral images (e.g. different number of wavebands or different positions of these bands or different bandwidth) and their combination with WLR imaging as well as various image analysis algorithms can be implemented without changing the hardware.

In alternative embodiments, different numbers of wavebands can be used for multi-spectral imaging. Either evenly or non-evenly spaced wavebands may be selected. These wavebands can be programmed into the system to realize multi-spectral reflectance imaging.

Figure 8:
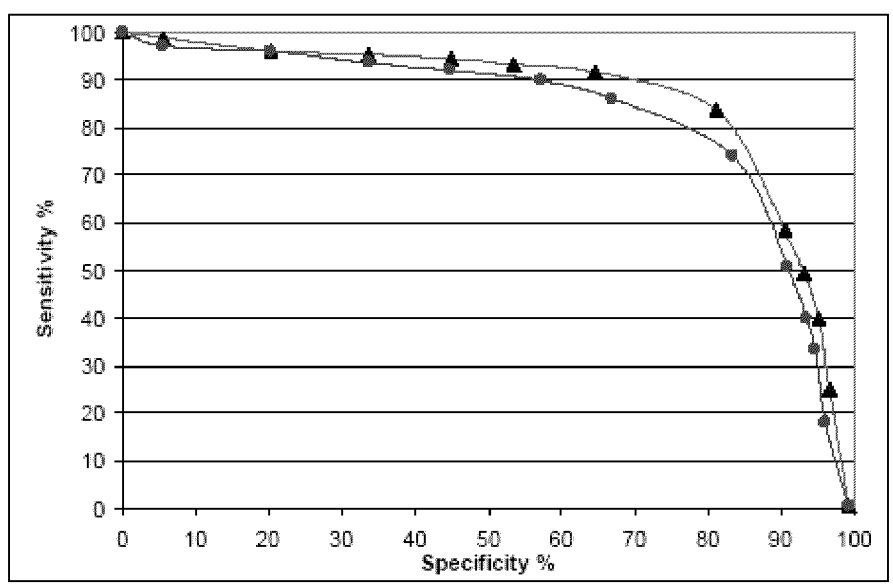
FIG. 8 is a graph of a ROC curve for 52 data points/wavebands spectral data (top triangle symbol curve) and the ROC curve for a reduced number of data points of 18 wavebands (lower circular symbol curve)

FIG. 8 shows a ROC curve for spectral data obtained from 52 data points/wavebands, (top triangle symbol curve) and an ROC curve when a reduced number of data points for 18 wavebands (lower circular symbol curve) is used. As shown, reducing the data points on each spectrum to 18 wavebands slightly reduces diagnostic accuracy but detection sensitivity and specificity remain reasonably good (80% and 77% respectively). Thus as shown, a multi-spectral reflectance imaging system, covering a reasonable number (e.g. 18+) wavebands, can provide superior accuracy comparing to the existing imaging endoscopy modalities, namely WLR mode and FL mode.

Selection of Optimized Wavelength Bands

Modeling and statistical approaches may be applied to determine the optimized wavelength bands for spectral imaging. A spectral analysis algorithm based on an optimized light-transport model is implemented in programmable image acquisition and processing electronics and a PC computer equipped with GPU for both real-time data processing and offline analysis. The minimum number of wavelengths and the optimum wavelength positions and band width are determined from empirical and/or simulated spectral measurements using optimization functions. One approach is based on numerical optimization (least-square) of an error function between an estimate obtained using the full spectrum and an estimate obtained using a spectrum that has been optimized for a reduced number of bands.

As an example, three different optimization functions are used for selecting the optimum number of wavelength bands and their band width and central wavelength positions:

1. Minimizing an error between disease classification (benign vs. malignant) accuracy obtained using the continuous full spectral measurement (C_f) and the classification accuracy obtained using a spectral measurement with n number of bands (C_n).
2. Minimizing an error between the optical properties obtained from the continuous full spectral measurements (OP_f) and that obtained from a spectral measurement with n number of bands (OP_n).
3. Minimizing an error between the spectral line shape of the continuous full spectra (S_f) and the spectral line shape of the spectra with n bands (S_n).

Figure 9:
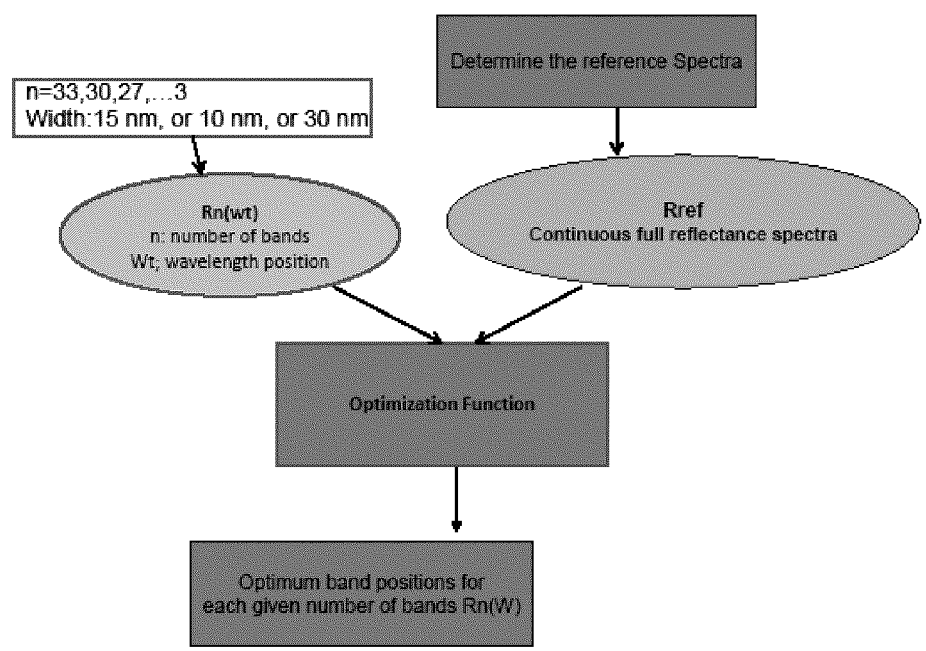
FIG. 9 is a flow chart illustrating an optimization procedure according to an example embodiment.

A flowchart illustrating an optimization procedure for obtaining optimum wavelength positions, Rn, for each given band number and given band width is shown in FIG. 9. A selection of a number of wavelength bands (n), width, and position (Wt) are used to generate a corresponding spectrum. The generated spectrum is compared to full spectral measurements (Rref) using the optimization function. The process is repeated for another selection of number of wavelength and band width, the output of the optimization function is recorded and compared to determine the final selection. In some embodiments the analysis may be done assuming that the total number of bands and band width, for each of the three spectral detection channel of interest (Blue 400-500 nm, Green 500-600 nm, and Red/NIR 600-800 nm), are equal.

The results of the above analysis may be used to generate graphs showing the relations between the number of wavelength bands, the band width, and the wavelength positions on the accuracies of the approximations. The generated graphs may be used for selecting the optimum design parameters (number of bands, their central wavelengths, and the band width) of the optical filters used in our spectral imaging device.

FIG. 10 shows an example accuracy comparison of the three approaches of optimization procedure and FIG. 11 shows the effect of the band width on the accuracy.

Mapping Algorithm

Figure 12:
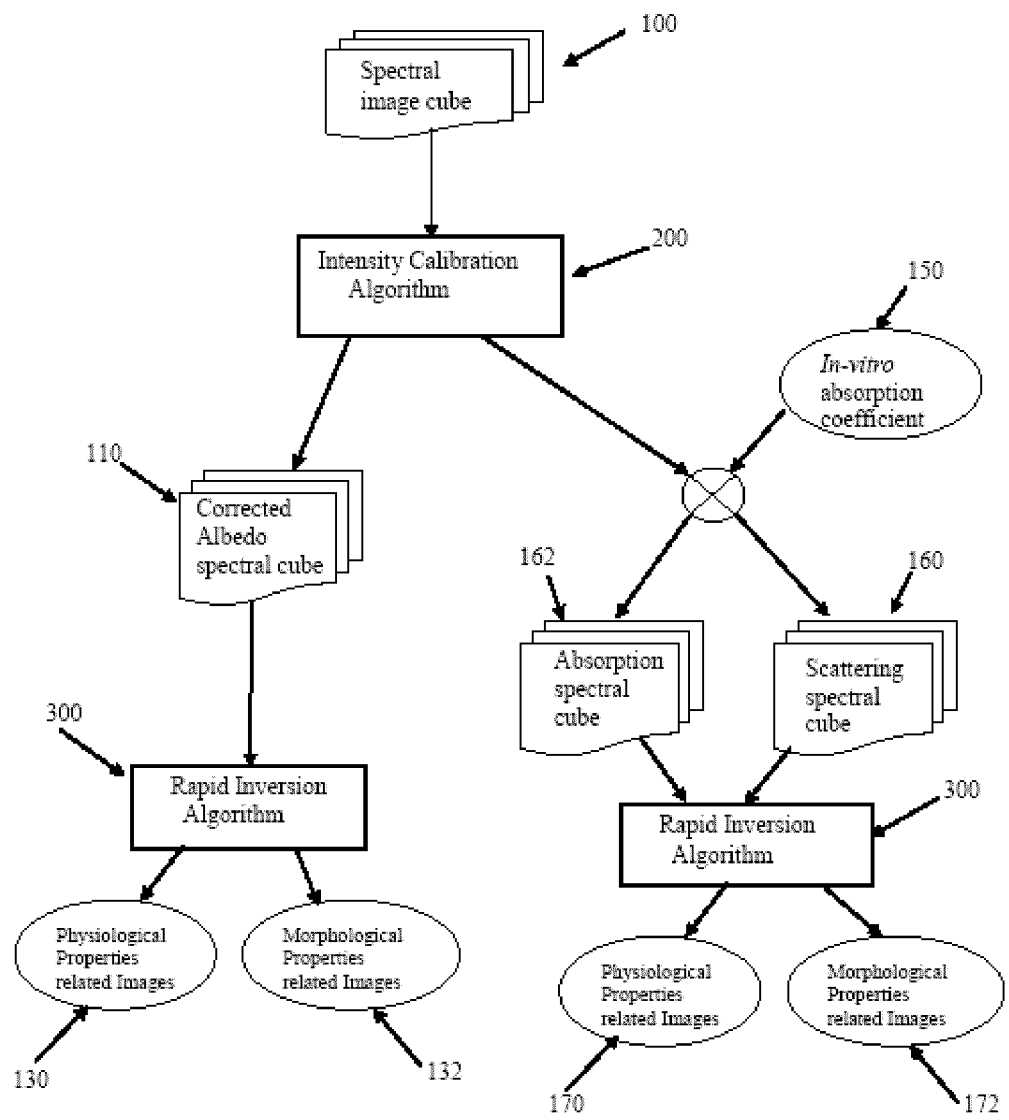
FIG. 12 is a flow chart illustrating a mapping algorithm according to an example embodiment.

A mapping algorithm is used for obtaining a plurality of tissue physiological (absorption) properties related images and a plurality of tissue morphological (scattering) properties related images. The mapping algorithm may comprise two components: an intensity calibration algorithm and a rapid inversion algorithm. FIG. 12 shows a block diagram of an example mapping algorithm that may be applied for generating tissue physiological and morphological images at video-rate.

The intensity calibration algorithm 200 can produce a corrected albedo spectral image 110, a scattering spectral image 160 and an absorption spectral image 162 from the obtained spectral images 100. The scattering spectral image 162 and the absorption spectral image 160 are then fed into the rapid inversion algorithm 300 to quantify the related tissue physiological and morphological properties 170 and 172.

In one embodiment, the in-vitro absorption spectra 150 of the tissue, as a priori known parameter, is used together with the corrected albedo spectral image 110 to obtain corrected absorption and scattering images 160, 162.

In another embodiment, the intensity calibration algorithm 200 first generates the corrected albedo spectral images 110, which are actually ratio of the absorption to the reduced scattering coefficients along the full spectral range. The corrected albedo spectral images 110 are then fed into the rapid inversion algorithm 300 to produce tissue physiological and morphological images 130, 132.

Note that the physiological and morphological parameters 130, 132 will have different accuracies from the physiological and morphological parameters 170, 172 since they are generated with different modeling approaches.

Figure 13:
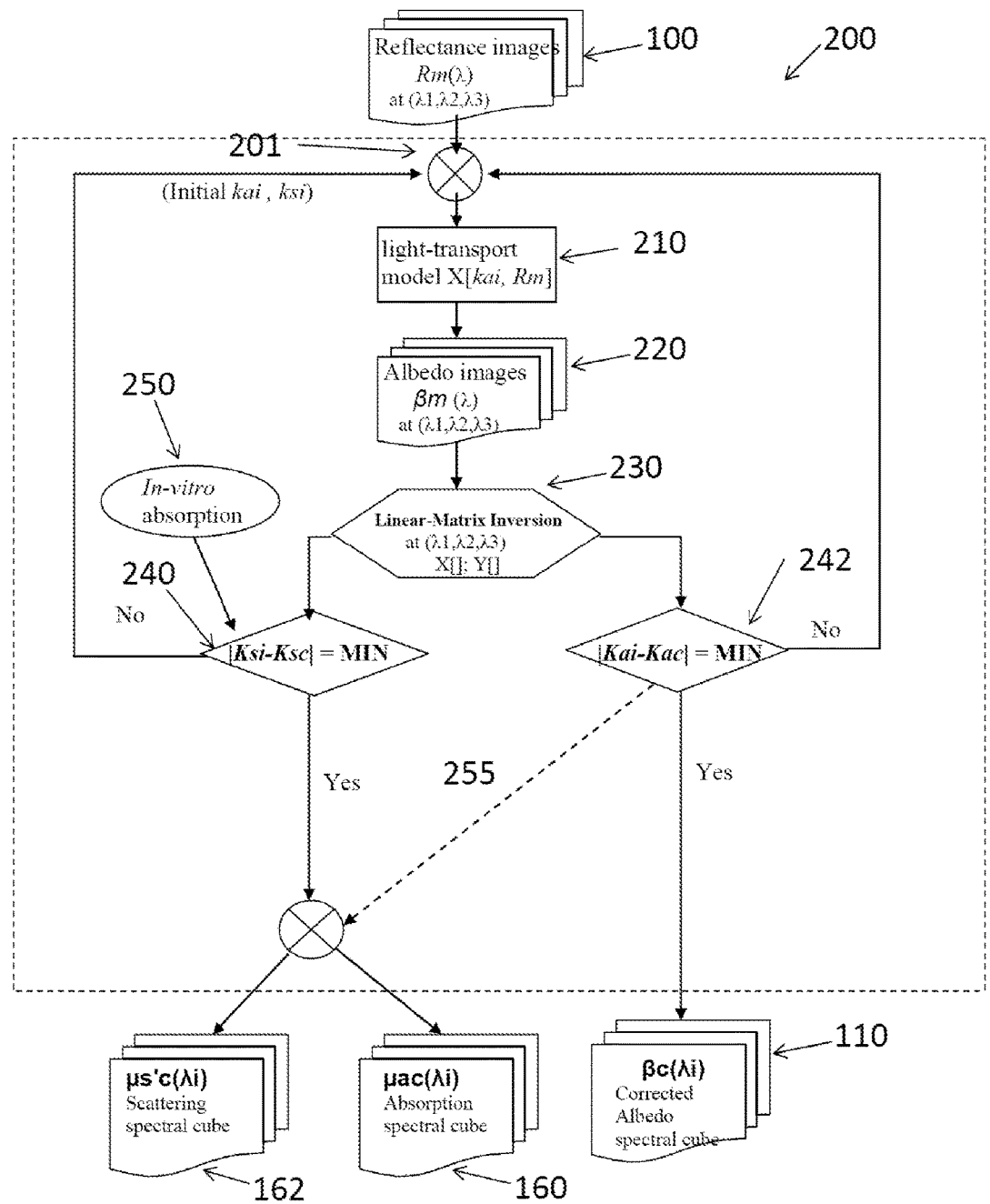
FIG. 13 is a flow chart illustrating an intensity calibration algorithm according to an example embodiment which may be used to correct spectral images for measurement geometry variations.

An example intensity calibration algorithm is shown in greater detail in FIG. 13. Intensity calibration algorithm 200 may be used to correct the intensity of the spectral images to account for measurement geometry variations such as, e.g., the variation in the coupling of reflected light from the tissue into the camera relative to the coupling of reflected light from a reflectance standard into the camera. For that respect, two intensity calibration constants are defined and formulated: (1) a measurement geometry constant (Ka), which can correct for the coupling angle and measurement distance variation between the tissue and the camera during the measurements; and (2) an albedo correction constant (Ks), which corrects for the relative intensity nature of the measurements and allows for deducing both the absorption image and the scattering image from the albedo image using the in-vitro absorption spectra of the tissue being imaged as a priori known input to the calibration algorithm.

The calibration constants may be related to the measured reflectance spectra by the following relations:

$$R_c(\lambda i) = K a R_m(\lambda i) \qquad (1)$$

$$\beta_c(\lambda i) = X[K a R_m(\lambda i)] \qquad (2)$$

$$\mu a_c(\lambda i) = Y[K s, \beta_c(\lambda i)] \qquad (3)$$

where $\mu s'_c(\lambda i) = \mu a_c(\lambda i)/\beta_c(\lambda i)$ where, $R_m$ and $R_c$ are the measured and corrected reflectance respectively; $\beta c$ and $\beta m$ are the corrected and measured albedo (ratio between the measured absorption and measured scattering coefficients) respectively; and $\mu a_c$ and $\mu s'_c$ are the corrected absorption and scattering coefficients respectively. X[ ] is an inverse light transport model/function that relates the corrected $\beta c$ albedo to the measured reflectance $R_m$, and Y[ ] is a function that relates the absorption amplitude to the scattering amplitude. The exact shape or mathematical formulation of X and Y functions depend on the light transport model used in the analysis. A number of known light transport models such as, e.g., Monte Carlo, diffusion approximation model, etc., can be used with the intensity calibration algorithm described herein.

For an example only, when a 1-D diffusion approximation model is used, a mathematical formulation of the X[ ] function may be as follows:

$$d_1 \beta_c(\lambda i)[(1+\beta_c(\lambda i))]^{1/2} - d_2[1+\beta_c(\lambda i)]^{1/2} + d_3 \beta_c(\lambda i) - d_4 = 0$$

where,
$d_1 = A' + 2AKaR_m$
$d_2 = 4AKaR_m$
$d_3 = 3A + 2A^2 KaR_m$
$d_4 = 4A^2 KaR_m$ where A is a constant which depends on the tissue refractive index and $A' = 1 + \tfrac{2}{3}A$.

The intensity calibration algorithm is applied along three wavelengths to produce corrected albedo spectral image or absorption spectral image and scattering spectral image in the full spectral imaging range. The physical meaning of the corrected absorption and/or scattering images means an image that is corrected from the reflectance intensity-related distortion/effect that resulted from the variation in the coupling of reflected light from tissue into camera relative to coupling of reflected light from reflectance standard into camera and relative to any movement of the light-camera probe (endoscope tip) orientation to tissue during measurements, which typically occurs during non-contact spectral reflectance measurements such as non-contact reflectance imaging. The algorithm can use in-vitro absorption spectra of the tissue being investigated as an a priori known parameter in order to generate the corrected absorption and scattering images along the full spectral imaging range. The fixed in-vitro absorption coefficient used in the intensity calibration algorithm (during the iteration/least-square procedure) acts as an internal tissue standard to allow for specifying and separating the scattering amplitude and the absorption amplitude. Consequently, it provides more robust quantitative data about tissue physiological and morphological properties.

As shown in FIG. 13, intensity calibration algorithm 200 uses three spectral images at wavelength λ1, λ2, λ3 (101), in-vitro absorption coefficients at λ1, λ2, λ3 (250) of the tissue being imaged, and randomly chosen initial values for measurement geometry constant Kai and albedo correction constant Ksi (201), as input parameters. The algorithm proceeds iteratively (240 and 242) until the calculated geometry constant Kac and the calculated albedo correction constant Ksc converge. The calculated albedo correction constant (Ksc) and geometry constant (Kac) can be used for producing in real time absorption spectral images 160 and scattering spectral images 162, or corrected albedo spectral images 110, respectively. The intensity calibration algorithm can be used with any light transport model such as diffusion approximation, a Monte Carlo generated look up table, or other light transport models.

In one embodiment, the calculated albedo correction constant (Ksc) and geometry constant (Kac) are used for producing in real time corrected absorption spectral images 162 and scattering spectral images 160 (arrowhead dash lined path 255 of FIG. 13).

In another embodiment, the intensity calibration algorithm generates only corrected albedo spectral images 110, along the full spectral range without the use of any priori information.

Figure 14:
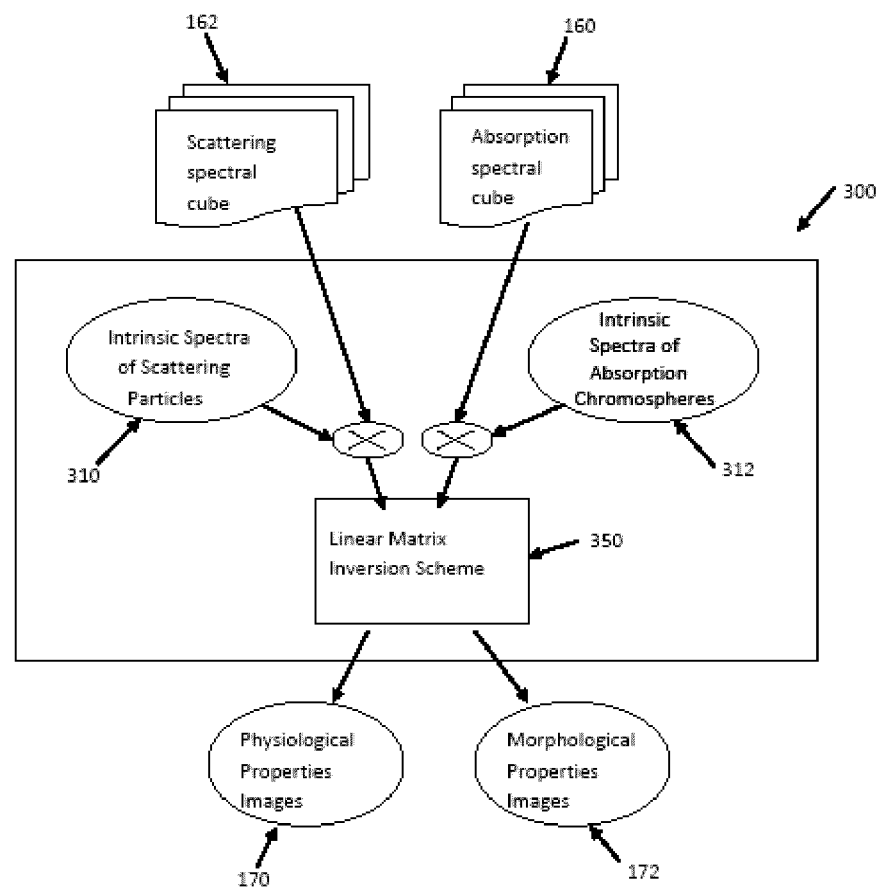
FIG. 14 is a flow chart illustrating a rapid inversion algorithm according to an example embodiment which may be used for quantifying tissue physiological and morphological properties.

An example rapid inversion algorithm is shown in FIG. 14. Rapid inversion algorithm 300 quantifies the related physiological and morphological properties 170, 172 from the absorption and scattering spectral images 160, 162 using linear matrix inversion scheme 350, and intrinsic spectra of tissue absorption chromophores 310 and tissue scattering particles 312, which are known standards.

Figure 14A:
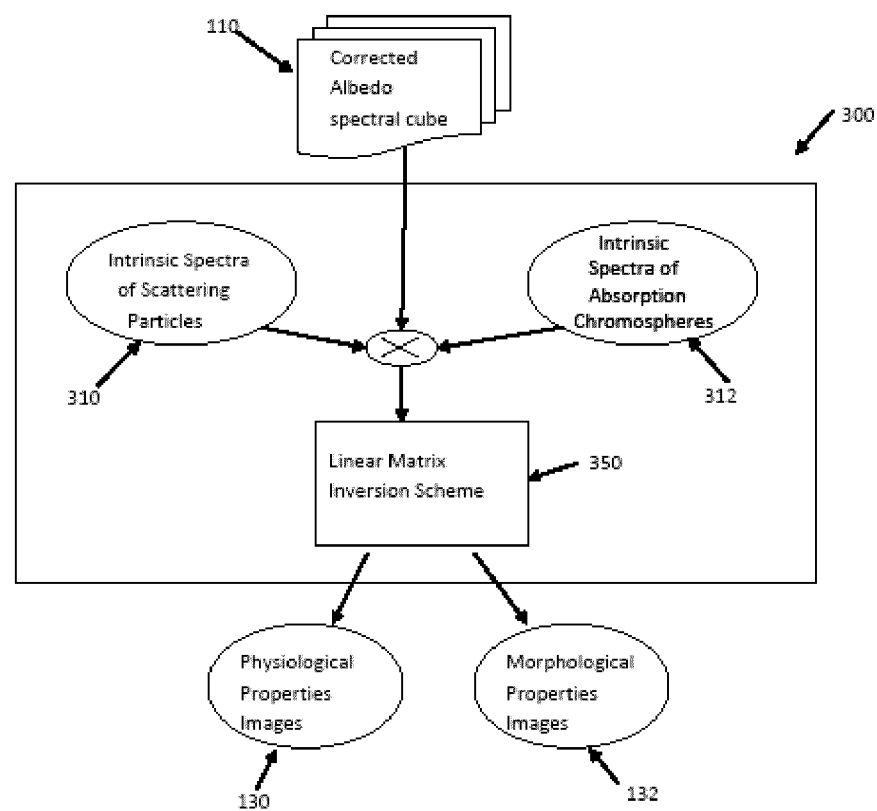
FIG. 14a is a flow chart illustrating a rapid inversion algorithm according to another embodiment of the present invention.

FIG. 14a illustrates an alternative rapid inversion algorithm 300. Rapid inversion algorithm 300 quantifies the related physiological and morphological properties 130, 132 from the corrected albedo spectral images 110 using linear matrix inversion scheme 350 and intrinsic spectra of tissue absorption chromophores 310 and tissue scattering particles 312.

The physiological images/maps that are generated can include an oxygenated hemoglobin concentration image, a de-oxygenation hemoglobin image, a total hemoglobin concentration, and/or a tissue water volume image for example. The morphological images that can be generated can include a scattering volume image, a mucosa layer thickness image, and a specific scattering particles volume fraction (such as nucleus volume fraction). The quantification of physiological and morphological tissue properties from the corrected absorption and scattering images directly (without the use of any radiative transport model) by using linear matrix inversion scheme, is advantageous as it provides for faster execution of the rapid inversion algorithm. In addition, use of such linear matrix inversion implementation can allow use of a parallel processing (such as GPU) more efficiently.

The following mathematical presentation describes the linear matrix inversion scheme used in a rapid inverse algorithm for obtaining the absorption spectral images:

$$\begin{pmatrix} C_1 \\ C_2 \\ \vdots \\ C_m \end{pmatrix}_{INV} = \left\{ \begin{bmatrix} I_{c1(\lambda_1)} & I_{c1(\lambda_2)} & \cdots & I_{c1(\lambda_n)} \\ I_{c2(\lambda_1)} & I_{c2(\lambda_2)} & \cdots & I_{c2(\lambda_n)} \\ \vdots & \vdots & \ddots & \vdots \\ I_{cm(\lambda_1)} & I_{cm(\lambda_2)} & \cdots & I_{cm(\lambda_n)} \end{bmatrix} \right\} \begin{pmatrix} \mu_{ac(\lambda_1)} \\ \mu_{ac(\lambda_2)} \\ \vdots \\ \mu_{ac(\lambda_n)} \end{pmatrix}$$

where, Cm is the m quantified physiological property, $I_{cm}(\lambda_n)$ is the intrinsic spectra of the chromophore m at $\lambda_n$, $\mu ac_{(\lambda_n)}$ is the corrected absorption coefficient at $\lambda_n$.

Similarly, the matrix below describes the matrix inversion scheme for obtaining the scattering spectral images:

$$\begin{pmatrix} S_1 \\ S_2 \\ \vdots \\ S_m \end{pmatrix}_{INV} = \left\{ \begin{bmatrix} I_{s1(\lambda_1)} & I_{s1(\lambda_2)} & \cdots & I_{s1(\lambda_n)} \\ I_{s2(\lambda_1)} & I_{s2(\lambda_2)} & \cdots & I_{s2(\lambda_n)} \\ \vdots & \vdots & \ddots & \vdots \\ I_{sm(\lambda_1)} & I_{sm(\lambda_2)} & \cdots & I_{sm(\lambda_n)} \end{bmatrix} \right\} \begin{pmatrix} \mu'_{sc(\lambda_1)} \\ \mu'_{sc(\lambda_2)} \\ \vdots \\ \mu'_{sc(\lambda_n)} \end{pmatrix}$$

where, Sm is the m quantified morphological property, $I_{sm}(\lambda_n)$ is the intrinsic spectra of the scattering particle m at $\lambda_n$. and $\mu sc(\lambda_n)$ is the corrected scattering coefficient at $\Lambda_n$. The mathematical formulation of $I_{sm}(\lambda_n)$ depends on the scattering particle model used to simulate the tissue scattering particles and components.

As shown in FIG. 14, the rapid inverse algorithm can take the absorption and/or scattering spectral images as inputs, and using the linear matrix inversion scheme and the intrinsic spectra of certain tissue chromophores and scattering particles, can generate a rapid mapping of certain physiological and/or morphological properties.

An example of the physiological and morphological parameters that can be mapped is shown in FIG. 15. FIG. 15 shows only one example of the resultant images such as, (a) oxygenation Image, (b) blood volume fraction image, (c) total scattering particles volume fraction image, and (d) detailed scattering particle volume fraction images (e.g. nucleus volume fraction), obtained during the rapid multi-spectral imaging.

The obtained multiple physiological and morphological images can be used for cancer detection and localization and tumor margin delineation, which in turn will benefit to therapy planning and monitoring.

While particular elements, embodiments and applications of the present disclosure have been shown and described, it will be understood, that the scope of the disclosure is not limited thereto, since modifications can be made by those skilled in the art without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another, or may be combined in various ways. All possible combinations and sub-combinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments. Indeed, the novel methods and systems described herein may be embodied in a variety of other forms; furthermore, various omissions, additions, substitutions, equivalents, rearrangements, and changes in the form of the embodiments described herein may be made without departing from the spirit of the inventions described herein.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The example calculations, simulations, results, graphs, values, and parameters of the embodiments described herein are intended to illustrate and not to limit the disclosed embodiments. Other embodiments can be configured and/or operated differently than the illustrative examples described herein.

The invention claimed is:

1. An apparatus for multispectral imaging of an object, the apparatus comprising:
   a light source configurable to emit light having a first spectrum characterized by a first set of a plurality of narrow bands, wherein the plurality of narrow bands in the first set are emitted simultaneously, the apparatus arranged to direct the light from the light source onto an area of the object; and,
   a multi-channel imaging light detector arranged to image the area of the object by obtaining reflectance imaging signals while exposing the object to the light having the first spectrum and configured to provide multi-channel image data based on the reflectance imaging signals; and
   an image processing system configured to extract a plurality of spectral images from the multi-channel image data, the plurality of spectral images comprising a spectral image corresponding to each of the plurality of narrow bands,
   wherein the image processing system comprises an intensity calibration algorithm operable to process the plurality of spectral images to yield one or more of corrected albedo spectral images and corrected absorption and corrected scattering spectral images, the intensity calibration algorithm being configured to correct an intensity of the plurality of spectral images to account for measurement geometry variations using a measurement geometry constant Ka and an albedo correction constant Ks,
   wherein initial input values of the measurement geometry constant Ka and the albedo correction constant are randomly chosen and the intensity calibration algorithm proceeds iteratively until a calculated geometry constant Kac and a calculated albedo correction constant Ksc converge, the calculated geometry constant Kac and the calculated albedo correction constant Ksc being applied for producing the at least one of the corrected albedo spectral images, or corrected absorption and corrected scattering spectral images.

2. An apparatus according to claim 1 wherein the light source is controllable to vary a spectrum of the light, the apparatus comprises a controller configured to switch the light source to emit light having a second spectrum characterized by a second plurality of narrow bands, the second plurality of narrow bands of the second spectrum occurring at wavelengths different from the first plurality of narrow bands of the first spectrum, and the controller is configured to operate the imaging light detector to obtain a first multi-channel image of the object while the light source is illuminating the area of the object with the light having the first spectrum and to operate the imaging light detector to obtain a second multi-channel image of the object while the light source is illuminating the area of the object with the light having the second spectrum.

3. An apparatus according to claim 1 wherein the light source has a plurality of illumination configurations, in each of the illumination configurations the light source is configured to emit light having a corresponding spectrum characterized by a corresponding plurality of narrow bands, such that, for each different one of the illumination configurations, the plurality of narrow bands occur at a corresponding different set of wavelengths.

4. An apparatus according to claim 3 wherein the apparatus comprises a controller configured to repeat, for each of a plurality of selected illumination configurations: switching the light source to the selected illumination configuration;

and operating the detector to obtain corresponding multi-channel image data while the light source is illuminating the area of the object with the light having the spectrum corresponding to the selected illumination configuration.

5. An apparatus according to claim 4 wherein the detector comprises an imaging array comprising an array of light-sensing elements overlaid by a pattern of colour filters, each of the colour filters passes light from two or more of the narrow bands in amounts determined by filter characteristics corresponding to the colour filters and the apparatus comprises a data store containing calibration information corresponding to each of the illumination configurations and an image processing subsystem configured to decompose the multi-channel image data using the corresponding calibration information to yield a plurality of narrow-band images corresponding to the plurality of narrow bands.

6. An apparatus according to claim 5 wherein the plurality of narrow bands consists of three narrow bands and the three narrow bands include a first narrow band in a blue wavelength range, a second narrow band in a green wavelength range and a third narrow band in a red/near infrared wavelength range.

7. An apparatus according to claim 1 wherein the light source comprises a broadband light source and a filter wheel comprising a plurality of filters, each of the plurality of filters having a corresponding filter function comprising a plurality of narrow pass bands.

8. An apparatus according to claim 7 wherein the broadband light source comprises a Xenon lamp.

9. An apparatus according to claim 1 wherein the light source comprises a plurality of narrow-band light emitters.

10. An apparatus according to claim 9 wherein the narrow band light emitters comprise semiconductor light emitters.

11. An apparatus according to claim 10 wherein the narrow band light emitters comprise light-emitting diodes.

12. An apparatus according to claim 1 wherein the light source comprises a broadband light source and one or more tunable filters.

13. An apparatus according to claim 12 wherein the tunable filters comprise acousto-optic tunable filters or liquid crystal tunable filters.

14. An apparatus according to claim 1 wherein the light source comprises a digital micromirror device based spectrally programmable light source.

15. An apparatus according to claim 1 wherein the plurality of narrow bands are in that portion of the electromagnetic spectrum consisting of visible and near infrared light.

16. An apparatus according to claim 1 wherein the plurality of narrow bands have wavelengths in the range of 390 to 1000 nm.

17. An apparatus according to claim 16 wherein the plurality of narrow bands have wavelengths in the range of about 400 nm to about 800 nm.

18. An apparatus according to claim 1 wherein the imaging detector comprises a plurality of light-sensing arrays each responsive to light in a corresponding pass band.

19. An apparatus according to claim 18 wherein each of the narrow bands of the plurality of narrow bands falls within a different one of the pass bands.

20. An apparatus according to claim 1 wherein the detector comprises an imaging array comprising an array of light-sensing elements overlaid by a pattern of colour filters.

21. An apparatus according to claim 20 wherein each of the colour filters passes light from two or more of the narrow bands in amounts determined by filter characteristics corresponding to the colour filters.

22. An apparatus according to claim 21 comprising a data store containing calibration information wherein the image processing system is configured to decompose the multi-channel image data using the calibration information to yield a plurality of narrow-band images corresponding to the plurality of narrow bands.

23. An apparatus according to claim 1 wherein a number of the narrow bands is equal to a number of channels of the multi-channel imaging detector.

24. An apparatus according to claim 1 wherein the image processing system further comprises a rapid inversion algorithm to derive at least one of: a physiological image of the object and a morphological image of the object based on one or both of the corrected albedo spectral images and the corrected absorption and corrected scattering spectral images.

25. An apparatus according to claim 24, wherein the physiological image comprises at least one of: an oxygenated hemoglobin concentration image, a de-oxygenated hemoglobin image, a total hemoglobin concentration image and a water volume image.

26. An apparatus according to claim 24 wherein the morphological image is based on at least one of: a scattering volume image, a mucosa layer thickness image and a scattering particle volume fraction image.

27. An apparatus according to claim 1 wherein the apparatus is configured as an endoscope.

28. An apparatus according to claim 27 wherein the light source is at a proximal end of the endoscope and the endoscope comprises a light guide connected to carry light from the light source to a distal end of the endoscope.

29. An apparatus according to claim 28 wherein the imaging detector is located at the distal end of the endoscope.

30. An apparatus according to claim 27 wherein the light source is located at a distal end of the endoscope.

31. An apparatus according to claim 30 wherein the light source comprises a plurality of light-emitting diodes arranged around an aperture for the imaging detector.

32. An apparatus according to claim 1 wherein the narrow bands have bandwidths of 20 nm or less.

33. An apparatus according to claim 1 wherein the apparatus is configured to obtain the spectral images at a rate of 24 or more sets of spectral images per second.

34. An apparatus according to claim 1 configurable to provide a white light illumination configuration wherein the light source illuminates the area with white light and the detector obtains colour images of the area.

35. An apparatus according to claim 1 wherein the image processing system comprises a rapid inversion module for quantifying the at least one physiological image and at least one morphological image based on the corrected albedo spectral images or the corrected absorption and corrected scattering spectral images using a linear matrix inversion scheme.

36. A multi-spectral imaging method comprising:
exposing an area of an object to light having a spectrum comprising a plurality of narrow wavelength bands, the plurality of narrow wavelength bands in the spectrum illuminating the object simultaneously;
detecting, using a multi-channel imaging detector, reflectance imaging signals while exposing the object to the light of the plurality of narrow wavelength bands and acquiring image data comprising an image of the exposed object based on the reflectance imaging signals
extracting a plurality of spectral images from the image data, the plurality of spectral images comprising a spectral image corresponding to each of the plurality of narrow wavelength bands; and processing the spectral images using an intensity calibration algorithm to obtain one or more of: corrected albedo spectral images and corrected absorption and corrected scattering spectral images, the intensity calibration algorithm using a measurement geometry constant Ka and an albedo correction constant Ks to correct an intensity of the plurality of spectral images to account for measurement geometry variations by inputting randomly chosen initial values of the measurement geometry constant Ka and the albedo correction constant and proceeding iteratively until a calculated geometry constant Kac and a calculated albedo correction constant Ksc converge.

37. A method according to claim 36 comprising repeating exposing the area of the object and acquiring the image data a plurality of times wherein the method comprises changing the spectrum for different repetitions by changing wavelengths of the bands of the plurality of narrow wavelength bands.

38. A method according to claim 37 wherein exposing an area of an object to light comprises passing the light through a filter having a plurality of passbands corresponding to the plurality of narrow wavelength bands and the method comprises passing the light through a different filter for each of the repetitions.

39. A method according to claim 38 wherein the filters are mounted around a wheel and the method comprises rotating the wheel and coordinating operation of the imaging detector with rotation of the wheel to acquire at least one image using the imaging detector while light is exposing the object through each of the filters.

40. A method according to claim 36 wherein the wavelength bands are within a spectral range consisting of visible and near infrared light.

41. A method according to claim 36 comprising repeating the method at a rate of 24 Hz or more.

42. A method according to claim 36 wherein exposing an area of an object to light comprises passing the light through a filter having a plurality of passbands corresponding to the plurality of narrow wavelength bands.

43. A method according to claim 42 wherein extracting a plurality of spectral images from the image data comprises processing the image data using calibration data wherein the method applies different calibration data for images corresponding to each different one of the filters.

44. A method according to claim 36 comprising synthesizing a white light reflectance image from the spectral images.

45. A method according to claim 36 further comprising processing the spectral images using a rapid inversion algorithm to obtain one or more of: a physiological image of the object and a morphological image of the object.

46. A method according to claim 45 wherein the object comprises tissue and the physiological image comprises one or more of: an oxyhemoglobin image, a deoxyhemoglobin image, a tissue water volume image and an image of another chromophore distribution.

47. A multi-spectral imaging method comprising:

exposing an area of an object to light in N number of narrow wavelength bands and obtaining reflectance images of the object while the object is exposed to the light;

wherein the exposing is performed in a sequence of steps and each step comprises simultaneously exposing the object to light having a spectrum consisting essentially of a set of n number the N number of narrow wavelength bands at a time and obtaining an image of the object using a multi-channel imaging detector;

processing multi-channel image data from the multi-channel imaging detector to obtain spectral images corresponding to the N number of narrow wavelength bands, and correcting an intensity of the spectral images using a measured reflectance spectra from a pixel of the image and using an intensity calibration algorithm to obtain corrected albedo spectral images or corrected absorption and corrected scattering spectral images using a measurement geometry constant Ka and an albedo correction constant Ks.

48. A method according to claim 47 comprising repeating the method at a video rate and displaying the spectral images or images derived from the spectral images.

49. A method according to claim 48 wherein the video rate is a rate of at least 24 Hz.

* * * * *